United States Patent [19]

Pieters et al.

[11] Patent Number: 4,489,593
[45] Date of Patent: Dec. 25, 1984

[54] METHOD AND APPARATUS FOR DETERMINING THE AMOUNT OF GAS ADSORBED OR DESORBED FROM A SOLID

[75] Inventors: Wim J.M. Pieters, Morristown; William E. Gates, Somerset, both of N.J.

[73] Assignee: Omicron Technology Corporation, Berkeley Heights, N.J.

[21] Appl. No.: 416,164

[22] Filed: Sep. 9, 1982

[51] Int. Cl.³ .................................................. G01N 15/08
[52] U.S. Cl. ..................................... 73/38; 73/432 PS
[58] Field of Search ......................... 73/19, 38, 432 PS

[56] References Cited

U.S. PATENT DOCUMENTS

| | | | |
|---|---|---|---|
| 2,729,969 | 1/1956 | Innes | 73/38 |
| 3,222,133 | 12/1965 | Ballou et al. | 73/432 PS |
| 3,771,367 | 11/1973 | Lowell et al. | 73/432 PS |
| 3,850,040 | 11/1974 | Orr et al. | 73/38 |

OTHER PUBLICATIONS

"Adsorption Flow Apparatus for Particle Surface Area Determinations", Numec Instruments and Control Corp., pp. 1 and 2, May 3, 1965.
F. M. Nelsen et al., "Determination of Surface Area", Analytical Chemistry, vol. 30, No. 8, Aug. 1958, pp. 1387–1390.
Robert J. Farrauto, "Determination and Applications of Catalytic Surface Area Measurements", AIChE Symposium Series No. 143, vol. 70, pp. 9–22, Jan. 15, 1975.
D. Dollimore et al., "The BET Method of Analysis of Gas Adsorption Data and its Relevance to the Calculation of Surface Areas", Surface Technology, vol. 4 (1976), pp. 121–160.
H. Bosch et al., "Automatic and Low-cost Determination of BET Surface Areas", *Journal of Physics E. Scientific Instruments*, vol. 10, pp. 605–608, (1977).
Bhat, R. et al., "A Simple Continuous Flow Apparatus for the Determination of Surface Area of Powders", Indian Journal of Technology, vol. 14, pp. 170–171, Apr. 1976.
M. G. Farey et al., "Determination of Surface Areas by an Improved Continuous Flow Method", Analytical Chemistry, vol. 43, No. 10, Aug. 1971, pp. 1307–1310.

*Primary Examiner*—Stephen A. Kreitman

[57] ABSTRACT

Methods for determining the amount of a gas adsorbed or desorbed from a solid sample wherein a gas is introduced or withdrawn from a sample containing chamber at a substantially constant mass flow rate while measuring the pressure change within said chamber as a function of time is disclosed. An apparatus for conducting said method which uses a mass flow controller is also disclosed.

54 Claims, 9 Drawing Figures

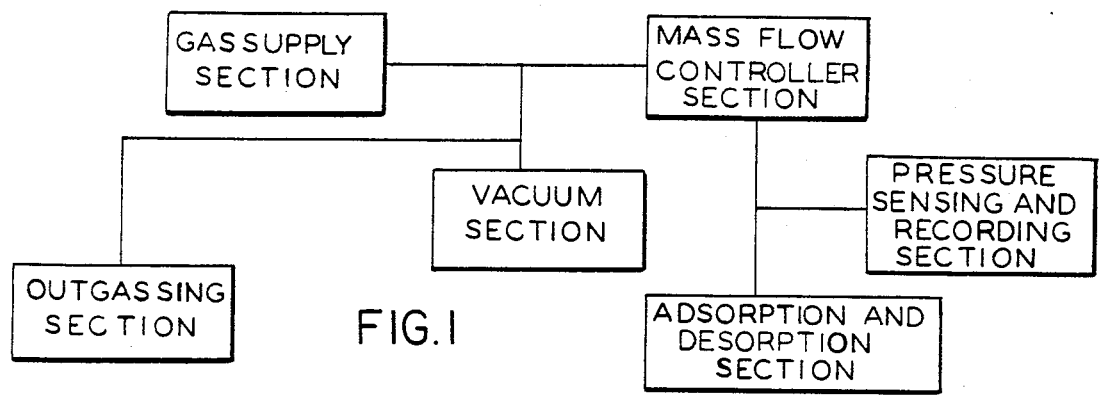
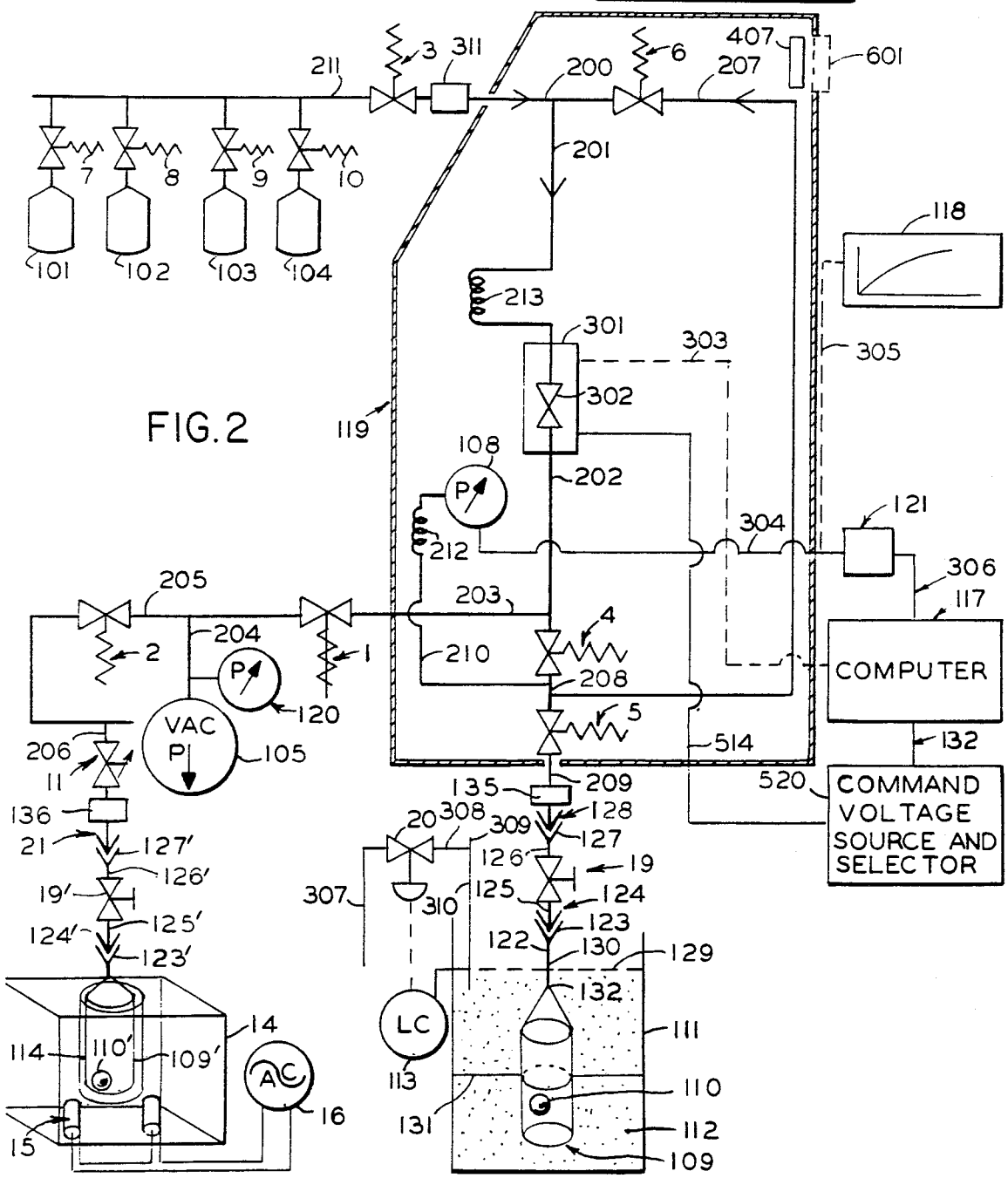

METHOD AND APPARATUS FOR DETERMINING THE AMOUNT OF GAS ADSORBED OR DESORBED FROM A SOLID

BACKGROUND OF THE INVENTION

The present invention relates to a method and apparatus for determining the amount of a gas adsorbed or desorbed by a solid in a manner such that the corresponding adsorption and/or desorption isotherm can be constructed from which in turn various morphological characteristics of the solid such as surface area, pore size distribution, and average pore volume, can be determined.

The measurement of morphological characteristics of solids, such as catalysts, catalyst supports, pigments, clays, minerals, and composite materials, has long been an outstanding goal of analytical chemistry.

For example, a very useful morphological characteristic of a solid is its surface area. One of the most widely used techniques for surface area determination is that of gas sorption. Gas sorption techniques utilize a theoretical model wherein the surface of the solid (i.e. the adsorbent) being characterized is viewed as being covered by a monolayer of closely packed molecules of an adsorbed gas (i.e. the adsorbate). If one can determine the amount (usually expressed in ml) of adsorbate in the monolayer, the area covered by the monolayer can then easily be calculated e.g. from the product of the number of molecules in the monolayer times the cross sectional area of each molecule. In 1938 Branauer, Emmett, and Teller described (J. Am. Chem. Soc. Vol. 60, 2309) a mathematical equation, referred to as the BET equation, for determining the amount of adsorbate in the monolayer from the absorption isotherm of the adsorbate. The absorption isotherm is a plot of the amount of the adsorbate adsorbed on a solid against either the relative pressure or the equilibrium pressure of the adsorbate at a constant temperature. In order to utilize the BET equation accurately to determine surface area, one must at least obtain a sufficient number of data points on the adsorption isotherm to be able to determine the point on the adsorption isotherm at which the "monolayer capacity" occurs. The "monolayer capacity" is a variable in the BET equation and represents the point on the adsorption isotherm wherein a monolayer of closely packed adsorbed molecules is present at the surface of the adsorbent. Since the monolayer capacity generally occurs at an adsorbate partial pressure of between about 0.8 and 2.5, one desires to known the adsorption isotherm at least over this range of partial pressures to be able to calculate the surface area from the BET equation. It is significant, however, that while the entire adsorption isotherm ranging from an adsorbate partial pressure of 0 to 1 (the adsorbate partial pressure is one way of expressing the equilibrium pressure of the adsorbate as a fraction of the pressure at which condensation of the adsorbate occurs under any set of constant volume and temperature conditions) need not be known for purposes of determining surface area alone, the information embodied in the entire adsorption isotherm is nonetheless very useful for other reasons as described hereinafter.

Thus, there is a strong incentive to develop analytical method which possess the capability of determining the entire adsorption isotherm.

Adsorption isotherms are conventionally determined by two general methods, namely, the gravimetric method, and the volumetric methods.

In the gravimetric method the amount of adsorbed gas at the equilibrium pressure is weighed with the aid of a microbalance. However, gravimetric methods possess the disadvantages of limitations in the choice of adsorbate (e.g. controlling a sample at liquid nitrogen temperatures is not feasible); effective temperature control of the sample is difficult to achieve; and sophisticated and expensive equipment is required to attain the high degree of sensitivity needed for the measurements. Volumetric devices, in contrast, are simpler and intrinsically more reliable.

In the volumetric method, the volume of the gas adsorbed in measured rather than the weight. Volumetric devices conventionally use nitrogen as the adsorbate at a temperature of $-195°$ C. These devices typically consist of a gas storage unit and a vacuum source unit connected in parallel to a volumetric measuring device, referred to as the doser unit, of known volume $V_1$; such as a burette or pipette. The doser unit can alternately be connected to either the vacuum unit or the gas storage unit by a series of stopcocks. The doser unit in turn is connected in series through another stopcock to a sample unit, i.e. a chamber of known volume $V_2$ which holds the solid to be tested. By manipulating the various stopcocks, the doser and sample units are evacuated, and the evacuated doser sealed off from the evacuated sample chamber. Nitrogen is permitted to slowly enter and fill the doser unit from the gas storage unit at which time the stopcocks are again manipulated to completely seal off the doser while the nitrogen pressure therein is measured. When a constant pressure, $P_1$, in the doser is achieved, the stopcock separating the sample chamber and doser is opened allowing the $N_2$ in the doser to expand into the sample chamber, the sample chamber and doser together defining a third Volume $V_3$ (i.e. $V_1 + V_2$). When the pressure in $V_3$ is constant, indicative of adsorption equilibrium, it is measured. This equilibrium pressure is used to calculate the total number of moles of $N_2$ that remains in the gas phase. The number of moles of $N_2$ adsorbed on the solid is equal to the moles of $N_2$ initially present in Volume $V_1$ of the doser plus the moles of $N_2$ in the sample chamber defining Volume $V_2$ (the moles in Volume $V_2$ for the initial run is 0 but increases with each successive run), less the moles of gaseous $N_2$ in Volume $V_3$, after equilibration. The combined data of the amount of $N_2$ adsorbed at a particular equilibrium pressure constitutes a single point on the adsorption isotherm. The above procedure is repeated each time to obtain additional points on the adsorption isotherm. Each successive run increases the pressure in the sample chamber until at atmospheric pressure, saturation of the sample solid which condensed $N_2$ occurs, i.e., condensation of $N_2$ takes place on the sample and the free space in the sample holder. Conventional practice is to generate about 8 data points on the absorption isotherm for surface area determinations. It generally takes one hour per data point to obtain pressure equilibration. Needless to say, this method is very time consuming, requiring 2 delays per data point waiting for equilibration, and the adsorption isotherm data points are generated on a discontinuous basis. A detailed summary of this method is provided in the review paper "The BET Method of Analysis of Gas Adsorption Data and Its Relevance To The Calculation of Surface Areas" by Dollimore, D., Sponner, P., and Turner, A., Surface Technology, Vol. 4, p. 121-160 (1976).

Discontinuous volumetric gas sorption units have been improved by automating the opening and closing of the stopcocks and by increasing the number of sample chambers and doser units. The time for equilibration has been shortened by experimentally determining equilibration times and programming the automated system to respond to a preset equilibration time. However, this does not alter the discontinuous nature of unit operations and still requires excessive waiting time to provide relatively few data points.

Bosch and Peppelenbos describe in the Journal of Physics E: Scientific Instruments, Vol. 10, p. 605-608 (1977) a dynamic method for determining data points on the adsorption isotherm. In accordance with this method a gaseous adsorbate is introduced into an evacuated sample chamber of known volume and temperature (e.g. liquid nitrogen temperature) at what is alleged to be a constant volume flow rate (e.g., about 1 cm$^3$ STP min$^{-1}$ at a partial pressure of about 0.25) while measuring the pressure. The alleged constant volume flow rate is achieved by introducing the adsorbate into the sample chamber through a capillary tube. The amount of adsorbate adsorbed by the adsorbent is calculated by comparing the pressure increase in the sample chamber in the presence of an adsorbing sample against time, with the pressure increase in a blank (i.e. a sample chamber having no adsorbing sample present therein) against time. In the presence of an adsorbent, the adsorbate gas will be partly adsorbed and it takes more time to reach a certain pressure than it does when using the blank. Thus, the volume of gas adsorbed by the sample (Va) at a particular pressure is calculated from the equation:

$$[V_a = \phi V(STP)\Delta t]_p$$

wherein $\phi V$ (STP) is the volume flow through the capillary tube (cm$^3$ min.$^{-1}$) at standard temperature and pressure, and $\Delta t$ is the extra time in minutes to reach pressure P compared to a blank experiment. While the volume flow rate is treated as being constant for purposes of a single data point on the adsorption isotherm, it is in fact acknowledged at page 608 that the flow rate is not constant, e.g. when nitrogen is employed as the adsorbate, thereby requiring much more laborious calculations to generate even a partial adsorption isotherm. Other disadvantages of this method stem from the use of a capillary tube to regulate flow. For example, the characteristics of a fixed capillary tube change with time and environmental conditions. Thus, fluctuations in ambient conditions induce fluctuations in the adsorbate flow rate as a result of thermoexpansion or contraction of the capillary tube. Fixed capillaries are not only difficult to manufacture within specified ranges but they are subject to plugging with solid adsorbent upon desorption and are so fragile that they need frequent replacement. A fixed leak capillary cannot be adjusted to control the flow of gas and provide optimum conditions dictated by the type of adsorbent sample being employed. More importantly, however, is the inaccuracy (e.g. 10-15% and higher) introduced into the adsorbtion isotherm and surface area determination of very high surface area materials, e.g. greater than 500 m$^2$/g if it is assumed that the volume flow rate is constant. This stems from the fact that the higher the surface area of the sample the longer it will take to achieve equilibrium pressure. Consequently, for a given weight of sample, the higher the surface area, the lower the flow rate must be, and the lower the flow rate the smaller the I.D. of the capillary tube must be, thereby enhancing the sensitivity of the flow rate to environmental fluctuations. Apart from the environmentally induced fluctuations in flow rate as described above, adsorbate backpressure, which builds up in the sample holder as one approaches higher partial pressures in the adsorbtion isotherm, also changes, i.e. reduces, the flow rate. It is admitted in Bosch et al pg. 606 that backpressure even at a partial pressure of about 0.2 results in a 0.6% decrease in the flow rate. Such backpressure induced volume flow fluctuations are magnified as one continues the collection of data points at higher points on the adsorbtion isotherm. Consequently, one is forced to accept increasingly larger experimental errors over the course of the experiment, or where possible mathematically compensate for such fluctuations by extremely complicated integration procedures with respect to the blank and the sample run.

In addition, there are intrinsic limitations in use of a capillary, stemming from the need to maintain the flow rate of the adsorbate to be not greater than the equilibration rate of adsorption, which prevent attaining a complete adsorption isotherm from a practical standpoint. For example, in a capillary system the flow rate is proportional to the pressure drop across the capillary. Consequently, since the initial flow rate is very low, backpressure reduces the flow rate even further so that after reaching about 70 to 80% of the adsorption isotherm, the flow rate becomes almost non-existent.

Innes, U.S. Pat. No. 2,729,969 discloses a capillary method very similar to Bosch et al. The system described therein has the same disadvantages discussed above attributable to the use of a capillary to regulate the flow of the adsorbate. Adsorbate introduction is conducted at a partial pressure regime of about 0.1 to 0.3 at a flow rate at about 7 to about 10 cc/min. It is acknowledged at col. 6, lines 45 et seq, that equilibrium pressure conditions did not exist at a flow rate of either 10 cc/min or 7 cc/min when employing small pore (hence high surface area) samples, i.e. the flow rate was greater than the adsorbate equilibration rate of adsorption. However, to obtain lower rates, either smaller diameter capillary tubes must be employed thereby increasing the sensitivity of the flow rate to environmental induced flow rate fluctuations or a lower fore pressure must be employed thereby increasing the sensitivity of the flow rate to backpressure induced flow rate fluctuations. At col. 4, lines 5 et seq it is stated that the flow rate is constant as shown at FIG. 4 therein. However, FIG. 4 of this patent illustrates a flow time of only 150 seconds using only 11 data points. Bosch et al also attempt to support allegations of constant flow rate with a similar plot using a flow time of 60 minutes and 6 data points. None of this data illustrate a constant flow rate over flow times of about 4 hrs. which are typically needed if the flow rate is to be maintained below the equilibration rate of adsorption of most samples of initially unknown surface areas for a time sufficient to achieve a partial pressure in the monolayer capacity range, e.g. 0.8-2.5. As stated above, environmental induced flow rate fluctuations accumulate over extended periods of time. Consequently, the data used to support allegations of constant flow rate for the capillary method do not reflect operating conditions that a commercially successful apparatus would be required to perform under.

Another significant disadvantage of the fixed leak capillary method develops if one attempts to employ the Bosch et al capillary system for determining desorption isotherms (the use of which is discussed hereinafter). In a desorption experiment, a preadsorbed gas would be removed from the surface of the sample through the capillary which is connected to a vacuum source. In this procedure the pressure in the sample holder decreases with time. Consequently, the pressure differential between both ends of the capillary is reduced over the course of the desorption experiment. Since this pressure differential is the driving force which removes the preadsorbed gas from the sample chamber, even a partial desorption experiment will take between about 20 and about 40 hours to complete. Accordingly, not only is the capillary desorption method time consuming, but the environmentally induced volume flow rate fluctuations accumulate over such extended periods, again necessitating complicated mathematical corrections to determine the actual volume flow rate (and therefore the actual amount of gas desorbed at any given equilibrium pressure) at any given time during the procedure. Such errors are not discussed in Bosch et al, since they are not concerned with desorption.

Innes does disclose the use of the capillary system for desorption. However, apparently because of the problems associated with evacuating a chamber through a capillary tube discussed above, he is forced to heat the nitrogen adsorbed on the sample at room temperature rather than desorb at liquid nitrogen temperatures. Taking the sample holder in and out of liquid nitrogen not only complicates the procedure, but it introduces significant error in the determination of the volume of the system which is under equilibrium conditions at, for example, liquid nitrogen temperatures. Such discontinuity causes the actual temperature of the sample to deviate from the liquid nitrogen temperature. A 1° C. variance in the actual sample temperature relative to the liquid nitrogen temperature will invalidate the test results.

In summary, neither of the capillary methods disclosed by Bosch et al and Innes disclose flow rates below 1 ml/min at STP, which are substantially constant as defined herein for any period of time.

Desorption isotherms are important because various mathematical equations are known which enable one to calculate the pore size distribution of a solid sample from the data embodied therein. A desorption isotherm is a plot of the amount of a preadsorbed gaseous material (referred herein as the desorbate) desorbed from a solid against the equilibrium pressure of the desorbate at a constant temperature. The desorption isotherm differs from the adsorption isotherm in that it is constructed starting with a solid saturated with the desorbate and gradually reducing the pressure over the solid to near absolute vacuum. In constrast, the adsorption isotherm starts with an evacuated solid sample and increases the pressure of a gaseous adsorbate in contact therewith until sample saturation is reached. The adsorption and desorption isotherms are collectively known as the sorption isotherm. Gas-solid interaction can cause at least a portion of the desorption path of the sorption isotherm to lie higher on the isotherm plot than the adsorption path. The failure of the desorption path to duplicate the adsorption path of the isotherm is commonly referred to as hysteresis. The two most common forms of hysteresis are referred to as closed loop and open loop. In the closed loop hysteresis behavior, the desorption path of the isotherm eventually rejoins the adsorption path at some low relative pressure. Closed loop hysteresis is normally associated with porosity in the sample being tested. For example, at the start of the desorption isotherm, the pores of the sample are saturated and filled with the desorbate. As desorption occurs, capillary action delays desorption of the desorbate present within the pores, such that a lower pressure is required to evacuate the pores relative to the pressure which initiated the filling of the pores during adsorption. This delay is expressed as closed loop hysteresis behavior of the sorption isotherm. Open loop hysteresis is characterized by the failure of the desorption path of the isotherm to rejoin with the adsorption path. Open loop hysteresis is usually associated with some measurable amount of irreversible adsorption, which typically occurs when the gas reacts with the solid sample upon adsorption, conventionally referred to as chemisorption. Consequently on desorption, less material will desorb than was initially adsorbed, giving rise to an open loop in the sorption isotherm.

By intentionally inducing chemisorption much can be learned about the surface of the solid sample. For example, chemisorption can be employed to determine the % dispersion and surface area of microscopic particles of a catalyst deposited on a support by employing a gaseous adsorbate which will undergo chemisorption with the catalyst particles but not the support.

Other information in the substantially complete sorption isotherm permits the determination of total pore volume, average pore size, and pore shape (e.g., slits vs. circular pores).

The above discussion highlights only a few of the incentives for obtaining substantially complete pictures of the entire sorption isotherm rather than narrow segments thereof, and any method or device capable of producing substantially complete sorption isotherms quickly and accurately possesses substantial advantages over capillary methods of the Bosch et al or Innes.

An alternative method for determining adsorption isotherms has been reported in an article by Nelsen, & Eggersten, Analytical Chem., Vol. 30 p. 13–87 (1958) titled "Adsorption Measurements By A Continuous Flow Method". In this method, nitrogen is adsorbed by the adsorbent at liquid nitrogen temperature from a gas stream of nitrogen and helium, and eluted upon warming the sample. The nitrogen liberated is measured by thermal conductivity. Thus, the amount of adsorbed gas is determined by concentration measurements in a continuous flow system at atmospheric pressure rather than by pressure volume measurements at below atmospheric pressure. This method is referred to herein as a chromatographic method for determining adsorption isotherms because of its resemblance to chromatography techniques. Two requirements of this method are steady flow of carrier and adsorbate gases, and through mixing of the two gases, insitu. In the Nelsen et al method, flow control is provided by capillary tubes. However in an article by Farey, and Tucker, Analytical Chem., Vol. 43, No. 10 p. 1307 (1971) titled "Determination of Surface Areas By An Improved Continuous Flow Method", the capillary tubes are replaced with a series of pressure and mass flow controllers in an attempt to achieve steady flow (see also, Bhat, R., and Krishnamoorthy, T., Indian Journal of Technology, Vol. 14, p. 170 (1976)). Nitrogen flow rates suitable for the experiment ranged from 2 to 20 ml/min. However, it is acknowledged at p. 1309 that flow rates through the detector would momentarily change during rapid temperature changes encountered in the adsorption/desorption cycle. This is not a problem in the Farey et al chromatographic method since each data point is generated on a discontinuous basis over a relatively short period of time (e.g. 20 min.) and it is within the capabilities of the mass flow controller to compensate for these fluctuations during the production of discontinous peaks, i.e. data points. The short duration needed for each peak also avoids the accumulation of error generated by environmental fluctuations over extended periods of time. In contrast, the method of the present invention cannot tolerate even minor uncontrolled fluctuations in the mass flow rate during the course of the analysis (e.g. about 4 hrs. for adsorption and 12 hrs. for desorption) except as defined hereinafter. The attainment of this goal in the present invention is even further complicated by the fact that mass flow rates in the range of 0.2 to 0.4 ml/min are typically employed. Such low flow rates are preferred to avoid administering or desorbing the gas to the adsorbent or desorbent respectively at a rate greater than the equilabration rate of adsorption or desorption, which typically is very low for high surface area materials. Low flow rates are particularly troublesome and cannot be achieved by conventional mass flow controllers at very low pressures where the thermal conductivity of the gases passing therethrough is very low. This stems from the fact that conventional mass flow controllers typically utilize the thermal conductivity of the gas passing therethrough as a way of metering the flow of the gas. This problem is exacerbated by environmental fluctuations in temperature which cause unwanted, uncontrolled, and accumulated fluctuations in the flow meter sensing elements of conventional mass flow controllers. Furthermore, the low thermal conductivity of gases at low pressure and low flow rates cause the environmentally induced fluctuations in the flow rate to impart a greater contribution to the total error in the flow rate relative to the use of conventional flow rates and pressures. Conventional mass flow controllers therefore are unsuitable for use in practicing the method of the present invention. Conventional flow meters and thermal valves which make up the primary components of a conventional mass flow controller are described in U.S. Pat. Nos. 3,650,505; 3,851,526; 3,938,384; and 4,056,975.

In view of the above, it is evident that there has been a continuing search for quicker, simpler, and more accurate methods and apparatus for determining sorption isotherms. The present invention was developed in response to this search.

SUMMARY OF THE INVENTION

In one aspect of the present invention there is provided a method for determining the amount of a gaseous adsorbate adsorbed by a solid absorbent which comprises:

(a) providing an evacuated chamber of known volume and maintained at a known temperature with an outgassed sample of adsorbent present therein;

(b) introducing gaseous adsorbate into said sample containing chamber at a known substantially constant mass flow rate for a time sufficient to obtain adsorption of at least a portion of said adsorbate by said adsorbent, said mass flow rate being not greater than the equilibration rate of adsorption of the adsorbate by the adsorbent and not greater than about 0.7 ml/min at standard temperature and pressure conditions;

(c) establishing the equilibrium pressure of said adsorbate as it is introduced into said chamber as a function of time, said equilibrium pressure being the sampled chamber pressure; and (d) correlating the adsorbate sampled chamber pressure, the adsorbate mass flow rate, and the time needed to attain said sampled chamber pressure with the amount of adsorbent adsorbed by the adsorbate at said sampled chamber pressure.

In another aspect of the present invention there is provided a method for determining the amount of desorbate desorbed as a gas from a solid desorbent saturated with condensed desorbate which comprises:

(a) providing a chamber of known volume and temperature with a previously outgassed sample of desorbent present therein having said desorbate condensed thereon and in equilibrium with a chamber atmosphere consisting of gaseous desorbate;

(b) withdrawing said desorbate from said chamber at a known, substantially constant mass flow rate which is not greater than the equilibration rate of desorption, of the desorbate from the desorbent for a period at least sufficient to desorb condensed desorbate from any pores of the sample;

(c) establishing the equilibrium pressure of said desorbate as it is withdrawn from said chamber as a function of time, said equilibrium pressure being the desorbate sampled chamber pressure; and (d) correlating the desorbate sampled chamber pressure, the desorbate mass flow rate, and the time needed to attain said sampled chamber pressure with the amount of desorbate desorbed at said sampled chamber pressure.

In still another aspect of the present invention there is provided an apparatus for determining the amount of a gas adsorbed by a solid adsorbent sample or desorbed from a solid desorbent sample which comprises:

(1) means for defining at least one chamber of known constant volume to contain said solid sample and a gas to be introduced into or withdrawn from said chamber means;

(2) means for continuously introducing a gas into or withdrawing a gas from said chamber means;

(3) means for establishing the pressure of said gas as a function of time within said chamber means as it is introduced or withdrawn therefrom;

(4) means for controlling the mass flow rate of said gas as it is being introduced or withdrawn from said chamber to be (a) substantially constant over the entire partial pressure range, of gas within said chamber, of at least from about 0.02 to about 1.0 and (b) not greater than the equilibration rate of adsorption of the gas by the adsorbent sample during said gas introduction, and not greater than the equilibration rate of desorption of the gas from the desorbent sample during said gas withdrawal;

(5) means for evacuating a gas from said chamber means and through said control means during withdrawal of said gas from said chamber means; and (6) means for maintaining a known temperature of gas within said chamber to be substantially constant.

BRIEF DESCRIPTION OF THE DRAWINGS

FIG. 1 is a block diagram of the preferred component sections of the apparatus of the present invention.

FIG. 2 is a schematic diagram of the component parts of each section as depicted in FIG. 1.

Figure 3:
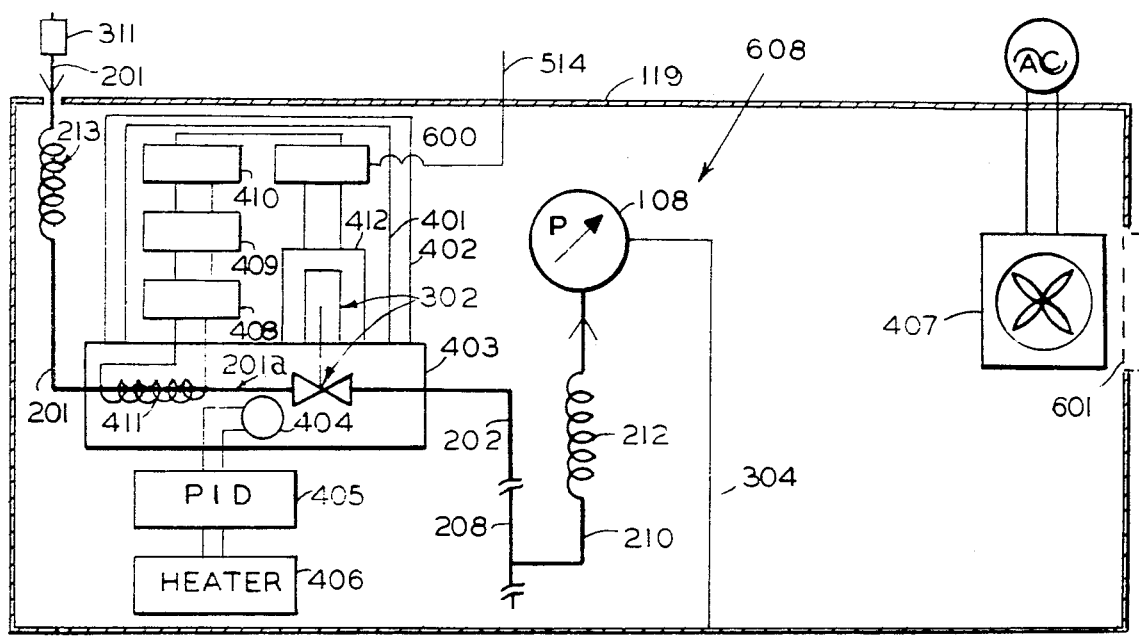
FIG. 3 is a more detailed schematic diagram of the component parts of the mass flow controller section present in box 119 of FIG. 2.

The diagrammatic showing of FIGS. 2 and 3 omit in certain instances features which those skilled in the art would recognize as desirable in actual apparatus operation. These omissions are made in order to simplify the presentation of the invention and to avoid encumbering it with well understood engineering details. Thus, for example, certain equipment obviously needed for a power supply, for electrical connections of selenoid valves, for computer automation, etc. are omitted from the diagrammatic representation.

DESCRIPTION OF PREFERRED EMBODIMENTS

The method of the present invention is characterized as being dynamic and volumetric. This method can be conducted in an adsorption mode, in a desorption mode, or a combination of the two wherein the adsorption mode is followed by the desorption mode.

The adsorption mode is conducted using a substance existing initially as a gas referred to herein as the adsorbate, and a solid referred to herein as the adsorbent or sample. During the course of the adsorption mode, the adsorbate is adsorbed by the adsorbent. The identity of the adsorbate will vary depending on whether the nature of the adsorption is intended and controlled to be physical or physical and chemical. It is known that adsorption phenomena may be the result of a physical or chemical process depending on the system involved and the temperature employed. Physical adsorption (frequently referred to as van de Waals' adsorption) is the result of a relatively weak interaction between solid and gas. One of the characteristics of this type of adsorption is that all the gas adsorbed by the solid can be removed therefrom by evacuation at about the same temperature at which it was adsorbed. Chemical adsorption or chemisorption (during which physical adsorption also takes place) involves a much stronger interaction between solid and gas than physical adsorption. A chemically adsorbed gas cannot be removed from the solid by evacuation at about the same temperature at which it was adsorbed, and evacuation at a temperature much higher than the adsorption temperature is required for the initial removal of chemisorbate. Typically, during chemisorption the adsorbent chemically reacts with the adsorbate. Thus, for physical adsorption, the adsorbate is selected in conjunction with the adsorbent to be chemically inert with respect thereto. Furthermore, since the quantity of physically adsorbed gas at a given pressure increases with decreasing temperature, the adsorbate is typically selected so that it will liquify at very low temperatures of typically from about $-195°$ to about $100°$ C. (e.g. $-195°$ to $0°$ C.). The adsorbates employed in the method of the present invention are conventional in gas sorption volumetric analytical methods.

Representative examples of adsorbates conventionally employed for physical adsorption include nitrogen, argon, hydrocarbons, e.g. butane, hexane, benzene, $H_2O$ and $CO_2$.

Representative examples of adsorbates referred to herein as chemisorbates which are conventionally employed to effect chemisorption include $O_2$, $CO$, $CO_2$, $H_2O$, $H_2$, and the like.

The identity of the adsorbent or sample can be any solid sought to be analyzed for its morphological characteristics, such as surface area. The methods described herein are applicable to sample having a surface area of typically from about 0.01 to about 1500, preferably from about 0.05 to about 1200, and most preferably from about 0.5 to about 800 $m^2/g$; and pore size radii of typically from about 5 to about 550, preferably from about 7 to about 450, and most preferably from about 9 to about 400 angstroms. The above pore size ranges reflect inherent limitations in the Kelvin equation described hereinafter.

Before determining the amount of adsorbate adsorbed by a sample, the sample is cleansed of impurities by removing adsorbed atmospheric gases (i.e. outgassed) such as nitrogen, oxygen, water vapor and the like. This is achieved by conventional methods as described in Orr, C. and Dallavalle, J. "Fine Particle Measurement" Macmillan Co., p. 164–204 (1960), the disclosure of which is herein incorporated by reference, such as for example by heating the sample in a vacuum at temperatures of about 110° to about 600° C. (e.g. 300°–400° C.) for a period of from about 4 to about 12 hrs (e.g. 8–12 hrs). The sample weight, and optionally density, is also determined in accordance with conventional methods before the sample is contacted with the adsorbate.

The apparatus in which the adsorption mode is conducted, as described hereinafter in greater detail, comprises a chamber which can be evacuated. The chamber can be characterized for purposes of description as comprising two portions, namely, a sample holder and the lines of the apparatus which communicate with the sample holder in an unrestricted manner during the experiment, through which the adsorbate is passed and introduced into the sample holder. The volume of the chamber is previously and accurately determined in accordance with conventional volumetric analytical procedures and the ideal gas law. This volume is preferably corrected for the volume of the sample, when present, based on the density of the sample by subtracting the volume of the sample from the volume of the chamber. However, when employing a high surface area sample having very small volume relative to the volume of the chamber, the sample volume can be ignored as a matter of convenience. When using the apparatus of the present invention, the sample holder can be sealed vacuum tight using a stopcock and is removably detachable from the line portion of the chamber. Thus, as a matter of convenience, weighing, outgassing and evacuation of the sample is normally conducted in the sample holder while disconnected from the chamber, and the sealed, evacuated sample holder thereafter connected with the line portion of the chamber. In accordance with conventional volumetric gas sorption analytical procedures, the volume of the sample holder is typically selected to be from about 10 to about 200 times the volume of the sample: to assure an accurate determination of the reference (blank) for both adsorption and desorption, to minimize error which can be introduced into the line volume value at the liquid bath-air interface by fluctuations in the liquid nitrogen level; and to minimize error in determining the density of the sample.

The temperature of the adsorbate is also known and preferably is constant during the experiment. The temperature of the adsorbate in the sample holder portion of the chamber is assumed to be the temperature of the sample holder portion of the chamber and is typically controlled to be within about 1° C. of the boiling point of the adsorbate at atmospheric pressure. Consequently, the temperature of the chamber sample holder is also determined. This is achieved by immersing a majority of the sample holder in a liquid bath of known, preferably constant temperature. As a matter of convenience, and to avoid the use of superatmospheric pressure, the temperature of the liquid bath is typically sufficient to cause condensation of the adsorbate at about atmospheric pressure. This is easily achieved by using liquid adsorbate at atmospheric pressure as the liquid bath which controls the temperature of the sample holder, or a specifically formulated liquid which boils at a temperature typically not greater than the boiling point of the adsorbate at atmospheric pressure. However, in some instances when the liquid bath is liquified adsorbate, impurities within the liquid bath may cause the bath temperature to be somewhat higher than the boiling point of the pure liquified adsorbate. As a result, the saturation pressure of the adsorbate (the pressure at which the adsorbate gas is in equilibrium with liquified adsorbate) may be above 1 atmosphere. The adsorbate is said to condense at about atmospheric pressure in this instance. The sample holder itself typically will also comprise two portions, namely, a relatively high volume portion which contains the sample, and a relatively low volume capillary neck. About half the capillary neck is immersed in the liquid bath and is considered to be at the liquid bath temperature, while the remainder of the capillary neck (which is at room temperature) becomes part of the line portion of the chamber when connected to the apparatus. The temperature of the line portion of the chamber is maintained constant by maintaining about 98% of the volume ($V_{C.T.}$) of the chamber line in a known and constant temperature controlled environment (e.g. about 39° C.), so that the adsorbate within this volume can be equated to the temperature of the controlled environment and is therefore also constant, $V_{C.T.}$ being the chamber line volume at constant temperature in the controlled environment. Pressure readings are then taken of the adsorbate in volume $V_{C.T.}$ and the temperature of the adsorbate in volume $V_{C.T.}$ is assumed to be in equilibrium with the adsorbate located in the 2% of the chamber line volume which is at room temperature ($V_{R.T.}$). Consequently, any fluctuations in the room temperature are thereby compensated for and disregarded. Thus, the temperature differential between the temperature of $V_{C.T.}$ and $V_{R.T.}$ is sufficiently small, the volume of $V_{C.T.}$ is sufficiently large relative to the total chamber line volume ($V_{C.T.}+V_{R.T.}$), and the total chamber line volume is sufficiently small relative to the total chamber volume, that this temperature differential is ignored and the temperature of $V_{C.T.}$ is equated to ($T_L$), the temperature of the chamber line volume ($V_L$) of Equations 1 to 3.

Thus, in this manner, an evacuated chamber of known volume and maintained at a known substantially constant temperature containing the outgassed sample can be provided. To this chamber is introduced, preferably continuously, the adsorbate at a known substantially constant mass flow rate preferably for a time sufficient to achieve an adsorbate partial pressure of at least 0.20 as defined hereinafter, and most preferably for a time sufficient to condense at least a portion of the adsorbate on the adsorbent (i.e. at a partial pressure of 1) while, establishing the pressure of the adsorbate within the chamber as a function of time as it is so introduced. This pressure is referred to herein as the sampled chamber pressure.

The term "substantially constant" as applied to the mass flow rate is defined herein to mean fluctuations, if any, of not greater than ±0.4%, preferably not greater than ±0.2%, and most preferably not greater than ±0.15% in the mass flow rate employed during the entire period of gas introduction and for substantially the entire period of gas withdrawal when the mass flow rate is not less than 0.2 ml/min; the phrase "substantially entire period of gas withdrawal" being defined hereinafter in relation to the partial pressure range withdrawal is operating within. When the mass flow rate is between about 0.05 and about 0.19 ml/min, the term "substantially constant" is defined herein to mean fluctuations, if any, of no greater than about ±1% in the mass flow rate. Mass flow rates below about 0.05 do not have practical utility since it would take a commercially unacceptable time to complete a run. The use of a substantially constant mass flow rate permits one to determine the mass flow rate as described hereinafter during the entire period during which the adsorbate is introduced into the chamber with an extremely high degree of accuracy not heretofore possible with conventional methods such as the capillary methods of Innes and Bosch et al.

The mass flow rate at which the adsorbate is introduced into the chamber is selected to be not greater than the equilibration rate of adsorption of the adsorbate by the sample. More specifically, for any given set of conditions of volume, temperature, pressure, and amount of adsorbate in contact with the sample, the rate at which the molecules of the adsorbate strike and are adsorbed by the sample will eventually equal the rate at which the adsorbed adsorbate molecules leave the surface of the sample. When this occurs, the rate of adsorption is referred to herein as the equilibration rate of adsorption.

At conditions of constant volume and temperature, the establishment of this equilibrium is observed by constant pressure (i.e. a fluctuation of not greater than ±0.25% of the pressure) of the adsorbate over a period of time, e.g. about 20 to 40 minutes. If the mass flow rate employed in the present invention is greater than the equilibration rate of adsorption and administration of the adsorbate is interrupted, it will take a finite period of time until the pressure in the chamber becomes constant. However, if the mass flow rate is not greater than the equilibration rate of adsorption and adsorbate administration is interrupted, the pressure will be constant from the time of interruption. By controlling the mass flow rate to be not greater than the equilibration rate of adsorption, the pressure established at any given time during the introduction of the adsorbate, will be the equilibrium pressure. This is significant because the adsorption isotherm is a plot of the amount of adsorbate adsorbed at a given equilibrium pressure. Consequently, the determination of the adsorption isotherm is simplified.

A mass flow rate capable of meeting the above equilibration rate limitation will be proportional to the weight of the sample. Furthermore, slightly higher mass flow rates can be employed for lower surface area samples than for higher surface area samples, since the equilibrium pressure is more quickly established for the former. In view of the above, mass flow rates, at standard temperature and pressure conditions, (S.T.P.) for a sample weight of from about 0.1 to about 1.0 g, will be not greater than about 0.7, preferably not greater than about 0.5, and most preferably not greater than about 0.4 ml/min and typically will vary from about 0.05 to about 0.7 (e.g. 0.05 to 0.19), preferably from about 0.2 to about 0.5, and most preferably from about 0.2 to about 0.4 ml/min. Since the surface area and porosity of the sample is often unknown, mass flow rates of less than 0.5 ml/min, typically 0.2 to 0.4 ml/min. have been found to be suitable for most samples. The flow rates described above are characterized as mass flow rates because the mass flow controller described hereinafter, responds to thermal conductivity of a gas which is proportional to the mass of the gas. Therefore milliliters per minute can be converted to mass by the Arrhenius equation.

As stated above, the adsorbate is preferably introduced into the chamber for a time sufficient to achieve an adsorbate partial pressure of at least about 0.20, when the objective is the determination of surface area. However, when a complete adsorption isotherm is desired an addsorbate partial pressure of at least 0.98 is required. The partial pressure ($P/P_s$) of the adsorbate is the chamber pressure (P) at any given time, e.g., during adsorbate introduction, divided by the pressure ($P_s$) of the adsorbate (under the chamber conditions of temperature and volume) at which liquefaction of the adsorbate occurs in the free space of the chamber, i.e. saturation pressure. The partial pressure is also referred to herein as relative pressure. At an adsorbate partial pressure above about 0.4, the linearity of the B.E.T. plot of equation 5, described hereinafter, derived from the adsorption isotherm, is gradually lost. Consequently, when the BET equation is to be used to determine surface area, it is preferred to utilize the data in the adsorption isotherm between adsorbate partial pressures of typically from about 0 to about 0.4, preferably from about 0 to about 0.35, and most preferably from about 0 to about 0.30. However, if other mathematical models are operative to determine surface area at higher adsorbate partial pressures in the adsorption isotherm, this data also would be useable. It is to be understood that the method described herein is capable of determining any amount of adsorbate adsorption, and the adsorbate introduction therefore must continue for a period at least sufficient to permit the sample to adsorb at least a portion of the adsorbate.

As also stated above, the adsorbate is most preferably introduced into the chamber for a time sufficient to condense at least a portion of the adsorbate on the sample. Condensation, which is the liquification of the adsorbate in the free space of the sample holder, is to be distinguished from adsorption. Adsorption occurs quickly after commencement of contact of the sample with the adsorbate. Condensation occurs in the presence of a sample as the atmosphere in the chamber begins to saturate with the adsorbate. Condensation therefore occurs at an adsorbate partial pressure ($P/P_s$) of 1. Thus, by continuing the adsorbate introduction until condensation, a complete adsorption isotherm can eventually be determined.

Accordingly, to achieve sufficient adsorption needed to attain a monolayer of adsorbate for surface area determinations the adsorbate is introduced into the chamber for a period sufficient to obtain an adsorbate partial pressure of typically greater than about 0.1, preferably greater than about 0.2, and most preferably greater than about 0.3 (e.g. greater than about 0.35), and typically will vary from about 0.2 to about 0.35, preferably from about 0.25 to about 0.35, and most preferably from about 0.30 to about 0.35. For a complete adsorption isotherm, adsorbate introduction is continued for a time sufficient to attain a partial pressure of typically greater than about 0.95, preferably greater than about 0.98 and most preferably 1. Generally, at the mass flow rates described herein, but converted to reflect actual use temperatures and pressures described herein, such partial pressures are achieved with continuous adsorbate introduction times of typically from about 2 to about 15, preferably from about 3 to about 12, and most preferably from about 4 to about 10 hrs.

The pressure of the chamber as the adsorbate is introduced is established by measuring the adsorbate equilibrium pressure as a function of time, e.g. starting from initiation of the adsorbate introduction. When operating at a mass flow rate of not greater than the equilibration rate of adsorption, the sampled chamber pressure will equal the adsorbate adsorption equilibrium pressure. The adsorbate equilibrium pressure is preferably measured enough times during the period of adsorbate introduction to permit construction of an accurate part of, or complete, adsorption isotherm. Typically this will involve establishing from about 100 to about 10,000, preferably from about 200 to about 2,000, and most preferably from about 300 to about 600 pressure data points during adsorbate introduction. It is even possible to measure the adsorbate adsorption equilibrium pressure continuously if desired. However, a frequency of pressure sampling of about 400 to 600 when operating within an adsorbate partial pressure range of about 0 to about 0.35 has been found to be most efficient for an adsorption mode BET surface area determination.

The mass flow rate is not necessarily known during adsorption of the adsorbate by the sample but is determined at some point before or after, preferably before, the sample adsorption run. The most convenient way for determining the mass flow rate is to run a blank wherein the adsorbate is introduced into the chamber in the absence of a sample, under the same conditions to be used in the presence of the sample, while measuring the chamber equilibrium pressure, referred to herein as the reference pressure, as a function of time. The mass flow rate can then be determined at standard temperature and pressure conditions from the equation:

$$MFR = \frac{273}{760} \cdot \frac{\Delta P}{t} \left( \frac{V_L}{T_L} + \frac{V_{S.H.}}{T_{S.H.}} \right) \quad \text{(Eq. 1)}$$

wherein MFR is the mass flow rate for the blank in ml/min; $\Delta P$(mm Hg) is the chamber pressure change during time interval (t), $V_L$ is the chamber line volume (cm$^3$) at temperature $T_L$; $V_{S.H.}$ is the chamber sample holder volume (cm$^3$) at temperature $T_{S.H.}$, $T_L$ is the chamber line temperature (°K.) of volume $V_L$ and $T_{S.H.}$ is the chamber sample holder temperature (°K.) of volume $V_{S.H.}$.

Time interval (t) is usually measured from the start of adsorbate introduction into the chamber to a time sufficient to cause the adsorbate to condense in the chamber. However, since the pressure/time relationship in a blank calibration run is linear at a substantially constant flow rate, time (t) need only be long enough to permit one to accurately extrapolate the pressure/time plot to the pressure at which adsorbate condensation occurs.

Once the mass flow rate is established by the blank, by using the same mass flow rate to determine the sampled chamber pressure/time relationship, the volume of adsorbate adsorbed ($V_{ads}$) can be calculated at any (t) during adsorbate introduction from the following equation:

$$V_{ads} = \frac{273}{760} \Delta P \left( \frac{V_L}{T_L} + \frac{V_{S.H.}}{T_{S.H.}} \right) - \Delta P' \left( \frac{V_L}{T_L} + \frac{V'_{S.H.}}{T'_{S.H.}} \right) \quad \text{(Eq. 2)}$$

wherein P, $V_L$, $T_L$, $V_{S.H.}$, and $T_{S.H.}$ are as described in connection with equation 1; P' is the change in sampled chamber pressure during the same time interval (t) used to determine P; $V'_{S.H.}$ is the sample holder volume corrected for the sample volume at temperature $T'_{S.H.}$, and $T'_{S.H.}$ temperature of the sample holder having the sample present therein and of volume $V'_{S.H.}$. When using a very low sample volume relative to the chamber volume, thereby permitting elimination of the correction for the sample volume, and a time interval starting from the initiation of the adsorbate introduction, equation 2 reduces to:

$$V_{ads} = \frac{273}{760} \left( \frac{V_L}{T_L} + \frac{V_{S.H.}}{T_{S.H.}} \right)(P - P') \quad \text{(Eq. 3)}$$

wherein P is the reference pressure, and P' is the sampled chamber pressure after time (t) of adsorbate administration, the remainder of said varables being as defined in equation 1. Other mathematical equations can be derived such as used by Bosch et al wherein the difference in time needed to attain a particular adsorbate equilibrium pressure in the presence and absence of a sample is employed to calculate the amount, e.g. Volume, of adsorbate adsorbed by the sample. In all instances, however, the amount, e.g. $V_{ads}$ is determined by correlating the adsorbate equilibrium pressure in the presence of a sample, the mass flow rate, and the time needed to achieve said adsorbate equilibrium pressure.

It is to be noted that during desorption, P' is greater than P, but the difference is assigned a positive value.

The desorption mode is the reverse of the adsorption mode. The desorption mode employs a solid, referred to herein as the desorbent or sample, the morphological characteristics of which are sought to be determined, and a gas or liquid referred to herein as the desorbate. The desorbate is evaporated from the sample during the desorption mode. Consequently, the desorption mode employs as a starting material, a sample which is first outgassed as described herein, and then its surface and any pores present therein contacted with an adsorbate in a manner sufficient to condense the same on the sample, fill the pores, and coat the outer surface of the sample with at least a monolayer of condensed desorbate. As a matter of convenience the sample is typically saturated with adsorbate to ensure complete filling of the sample pores. Upon condensing the gas on the sample, it is referred to herein as the desorbate. Thus, the term "desorbate" is used in place of "adsorbate" merely to identify the mode in which the gas or liquid constituting the same is employed, and the scope of materials which can constitute the adsorbate and desorbate is the same.

Accordingly, to conduct the desorption mode, a chamber of known, preferably known and constant, volume and temperature as described in accordance with the adsorption mode, is provided with a sample having desorbate condensed thereon and in equilibrium with a chamber atmosphere consisting of gaseous desorbate. This typically is performed by conducting the adsorption mode until sample saturation is achieved as described hereinabove. The desorbate is then withdrawn, preferably continuously, from the chamber at a known substantially constant mass flow rate for a period at least sufficient to desorb condensed desorbate from the sample, and preferably until complete removal of the desorbate from the sample. The term "substantially constant" when applied to the desorbate mass flow rate is defined herein to apply only at desorbate partial pressures ($P/P_s$) of not less than about 0.02, preferably not less than 0.03, and most preferably not less than about 0.04. At desorbate partial pressures of less than about 0.02 the mass flow controller described herein cannot maintain the mass flow rate substantially constant. However, this does not affect the accuracy of the results because no useable data is obtained at a partial pressure range of 0.02 to 0.

The mass flow rate of desorbate withdrawal is controlled (in a manner similar to the adsorption flow rate) to be not greater than the equilibration rate of desorption of the desorbate from the sample. The equilibration rate of desorption is the same as defined for the equilibration rate of adsorption, with the exception that the equilibrium is established under conditions of gas withdrawal from, rather than introduction into, the chamber. The use of these flow rates simplifies the procedure since the chamber pressure is the desorbate equilibrium pressure at any given time during desorbate withdrawal and it is the desorbate equilibrium pressure which provides data points for axis on the desorption isotherm.

Desorption mass flow rates at a sample weight of from about 0.05 to about 1.0 g, and at S.T.P. conditions, typically will be not greater than about 0.7, preferably not greater than about 0.5, and most preferably not greater than about 0.4 ml/min, and typically will vary from about 0.05 to about 0.7 (e.g., 0.05 to 0.19, and/or 0.2 to 0.7), preferably from about 0.2 to about 0.4, and most preferably from about 0.2 to about 0.3 ml/min.

Slightly higher desorption mass flow rates can be employed for less porous samples relative to samples of higher porosity, since the equilibration of pressure will occur more quickly for the former. When the porosity of the sample is unknown, desorption mass flow rates of less than 0.5 ml/min, typically 0.2 to 0.4 ml/min are suitable for most samples.

As stated above, the desorbate withdrawal is continued for a period at least sufficient to desorb condensed desorbate from the pores of the sample. In this regard, the comments distinguishing condensation from adsorption also apply to the desorption mode, i.e. complete desorption of desorbate from the sample surface (as distinguished from pores within sample) need not occur, since the desorption isotherm primarily on the sample porosity characteristics. By continuing desorbate withdrawal until condensed desorbate is removed from the pores of the sample, the critical information needed for determine the pore size distribution is obtained, if one makes a mathematical correction for the desorbate which remains adsorbed on the walls of the pores. As a matter of convenience it is desirable to remove all desorbate from the sample.

Desorption from the sample of condensed desorbate typically will occur at a desorbate partial pressure ($P/P_s$) of less than about 1.0, the desorbate partial pressure being the same as defined for adsorbate partial pressure. Accordingly, the desorbate is withdrawn from the chamber for a time sufficient to obtain a desorbate partial pressure of typically less than about 0.20, preferably less than about 0.10, and most preferably less than about 0.04, and can vary typically from about 1.0 to about 0.2, preferably from about 1.0 to about 0.1, and most preferably from about 1.0 to about 0.02. Generally at the desorption mass flow rates described herein converted to reflect actual use temperatures and pressures, such partial pressures are achieved with continuous desorbate withdrawal times of typically from about 8 to about 20, preferably from about 8 to about 16, and most most preferably from about 9 to about 14 hrs.

As with the adsorption mode, the chamber pressure in the presence of a sample, referred to herein as the desorption sampled chamber pressure, is established as a function of time during desorbate withdrawal. This is achieved by measuring the desorbate equilibrium pressure as a function of time, as it is so withdrawn, e.g. starting from initiation of desorbate withdrawal. Typically the desorbate equilibrium pressure is measured enough times during the period of desorbate withdrawal to permit construction of a part, preferably all, of an accurate desorption isotherm. Typically this will involve establishing from about 500 to about 40,000, preferably from about 1,000 to about 10,000, and most preferably from about 1,000 to about 5,000 pressure data points during desorbate withdrawal over the partial pressure ranges described above. A frequency of pressure sampling of about 2,000 has been found to be suitable for most samples for typical pore size distribution determinations.

As with the adsorption mode, the desorption mass flow rate is conveniently determined before or after conducting desorption mode in the presence of the sample, using a blank. Thus, an empty sample holder is saturated with condensed desorbate which is then withdrawn at the same desorption mass flow rate and conditions of temperature and volume to be used during the desorption mode while measuring the chamber pressure, referred to herein as the desorption reference pressure. The desorption mass flow rate can then be determined in accordance with equation 1 described above. The pressure/time relationship in the desorption blank calibration run is linear from a point after removal of desorbate which has condensed on the sample holder wall down to a partial pressure of about 0.02. Consequently, the duration of desorbate withdrawal (time (t) in equation 1) need only be long enough to permit accurate extrapolation of the blank pressure/time plot to the desorption sampled chamber pressure at which evaporation of condensed desorbate from the pores of the sample occurs, and preferably to the desorption sampled chamber pressure at which complete desorption occurs.

Once the desorption mass flow rate is determined, the use of this same flow rate to determine the desorption sampled chamber pressure/time relationship permits the calculation of the volume of desorbate desorbed ($V_{dsb}$) at any time (t) during desorbate withdrawal from equations 2 or 3 described above with appropriate substitutions, by correlating the desorbate equilibrium pressure in the presence of a sample, the desorption mass flow rate, and the time needed to achieve said desorbate equilibrium pressure.

From the Vads or Vdsb as determined above, the adsorption isotherm and/or desorption isotherm can be determined, e.g., for the adsorption isotherm, a plot of Vads on the Y axis and the corresponding relative pressure ($P/P_s$) on the x-axis (P being the adsorption equilibrium pressure and $P_s$ being the saturation pressure of the adsorbate at the chamber temperature) is constructed; while for the desorption isotherm, the adsorption equilibrium pressure (P) in the relative pressure ($P/P_s$) is replaced with the corresponding desorption equilibrium pressure. The information embodied in the adsorption isotherm can be used to determine the surface area of the sample by the B.E.T. equation; the information embodied in the desorption isotherm can be used to determine pore size distribution from the Kelvin equation, and the total pore volume ($V_p$) per gram of sample can be determined from the total volume at STP of desorbate adsorbed per gram of sample at saturation pressure ($V_s$), the molecular weight of the desorbate (M), the molar volume of the desorbate ($M_v$), and the density of liquid desorbate (D') in accordance with Equation 11.

The B.E.T. equation can be used to determine the B.E.T. surface area of a material. The B.E.T. equation typically is used between relative pressures of 0 to 0.35 for the determination of the internal B.E.T. surface area of a porous material. The linearized form of the B.E.T. equation is:

$$\frac{Pr}{V(1-Pr)} = \frac{1}{V_mC} + \frac{C-1}{V_mC} Pr \qquad (Eq.\ 4)$$

wherein Pr is the relative pressure ($P/P_s$), obtained from the adsorption isotherm; V is the volume at S.T.P. of the adsorbate adsorbed by the sample per gram of sample at relative pressure Pr; $V_m$ is the monolayer capacity of the adsorbate, i.e. the volume of adsorbate adsorbed as a monolayer on the sample; and C is the B.E.T. constant dependent on adsorption enthalpy.

Plotting the left hand side of equation 4 versus Pr should result in a straight line. From the slope and the Y intercept of this line $V_m$ can be calculated from:

$$V_m = \frac{1}{slope} + \frac{1}{intercept} \qquad (Eq.\ 5)$$

The specific B.E.T. surface area ($SA_{BET}$) can then be calculated from the equation:

$$SA_{BET} = \frac{V_m \cdot N_{av} \cdot S_{mol}}{V_{mol} \cdot W} \qquad (Eq.\ 6)$$

wherein $V_m$ is as described in equation 4; $N_{av}$ is Avogadro's number; $S_{mol}$ is the cross sectional area of the adsorbate molecule; $V_{mol}$ is the adsorbate molar gas volume at S.T.P.; and W is the sample weight. When it is assumed that the adsorbate molecules in the monolayer have the closest hexagonal packing, the cross-sectional area of an adsorbed molecule ($S_{mol}$) can be calculated from the following equation:

$$S_{mol} = 1.091[M/(N_{av})D]^{\frac{2}{3}} \quad \text{(Eq. 7)}$$

wherein M is the molecular weight of the absorbate; Nav is as described above; and D is the density of the adsorbate.

The Kelvin equation is used to calcuate the pore size distribution of a porous material. This equation gives the vapor pressure over a liquid contained in a pore (or capillary) as a function of the pore volume to surface area per gram ratio of the pore as follows:

$$\frac{dV}{dS} = - \frac{V_L (\sigma L) \cos \phi}{(R)(T)(\ln Pr)} \quad \text{(Eq. 8)}$$

wherein $V_L$ is the molar volume of liquid desorbate at S.T.P., $\sigma$ is the surface tension of the desorbate when in liquid form; R is the gas constant; T is the absolute desorbate temperature; Pr is the desorbate relative pressure; and $\phi$ is the angle of contact between the liquid desorbate and the pore wall.

If all pores are assumed to be circular and nonintersecting the following substitution may be made:

$$\frac{dV}{dS} = \frac{1}{2} R_k \quad \text{(Eq. 9)}$$

wherein $R_k$ is the Kelvin pore radius of the sample. For different pore systems other substitutions may be necessary as would be obvious to the skilled artisan. It is assumed the liquid desorbate in the pores wets the entire surface i.e. $\phi = 0$ and $\cos \phi = 1$. This is not unreasonable for desorption from a porous material. Accordingly, equation 8 may be written as follows:

$$\ln Pr = - \frac{(2)(V_L)(\sigma L)}{(R_k)(R)(T)} \quad \text{(Eq. 10)}$$

To calculate the pore size distribution, the volume of desorbate which is desorbed ($V_{dsb}$) at a particular pressure interval is determined from the desorption isotherm. The radius of the pores from which the desorbate desorbs in that pressure interval can be calculated from the Kelvin equation after correcting $R_k$ for the amount of desorbate which remains adsorbed on the walls of the pores having a thickness (t') from the equation $R_p = R_k + t'$ wherein t' is determined from the Halsey equation. Dividing the volume of desorbate desorbed by the difference in pore radius gives the frequency in the pore size distribution curve.

A distribution of the pore size (i.e. radius) s plotted using the value of $\Delta V_{dsb}/\Delta R_p$ as the y-axis and the corresponding value of $R_p$ in angstroms for the x-axis, and the area under each peak in the plot is integrated to determine the volume of pores at a particular radius $R_p$ per unit volume of sample. The correction in $R_k$ made for the amount of liquid desorbate which is adsorbed on the walls of the empty pores is described by Gregg & Sing, "Adsorption, Surface Area, and Porosity", N.Y. Academic Press, p. 152-165 (1967).

Total pore volume per gram of sample can be determined from the equation:

$$V_p = \frac{(V_s)(M)}{(M_v)(D')} \quad \text{(Eq. 11)}$$

the variables of which are described above.

It is to be understood that the present invention is not limited to any particular mathematical model for using the information embodied in either the adsorption or desorption isotherm, and such information can be manipulated as desired in accordance with any conventional procedure.

The method and apparatus of the present invention can also be employed to effect chemisorption. This is useful because it permits one to determine the surface area and/or dispersion of very small particles (such as particles which possess catalytic activity), and referred to herein as the chemisorbent or active phase, which have been deposited on larger particle (such as a catalyst support) and referred to herein as the support solid.

The dispersion of the active phase can be very useful in catalyst evaluations because it provides information about the number of catalytic sites available at the surface of the support. This area of analytical chemistry is well developed and the appropriate selection of a suitable chemisorbate, and the adsorption temperature, for use with a particular active phase is reviewed for example in Muller, J. Rev. Pure Appl. Chem., vol. 19, p. 151 (1969); Farrauto, R., AIChE Symp. Series, vol. 143, pp. 143, 70, 9-22 (1970) the disclosures of which are herein incorporated by reference. Active phases which can be effectively determined with the chemisorption method include Pt, Pd, Ni, Co, Cu, Ag and Fe, as well as a variety of metal oxides including $Cr_2 O_3$, CuO, NiO, sulfides, and the like. For example a suitable chemisorbate for a platinum catalyst is hydrogen which is reactive with platinum at temperatures of greater than about 0° C. Consequently the chemisorption sample holder temperature is controlled to be at least such temperature.

Accordingly, the chemisorption mode is conducted by selecting a suitable chemisorbate in conjunction with the active phase which will be present on the solid support, such that the chemisorbate will selectively chemisorb on the surface of the active phase but not the solid support. The weight percent of active phase deposited on the support should be known if the dispersion of the active phase is sought to be determined. The adsorption mode is conducted as described herein using a chemisorbate as the adsorbate and solid supported active phase as the sample. The chamber temperature is conventionally selected in conjunction with the chemisorbate-active phase reactive thresholds to assure chemisorption. Upon completion of the adsorption run, the total amount of chemisorbate physically and chemically adsorbed as a function of time is determined. During this adsorption run, the chemisorbate will not only be physically adsorbed but will also be irreversibly chemisorbed by the active phase to the extent that when the chamber is subsequently evacuated the chemisorbate will not desorb from the surface of the active phase. In contrast, the chemisorbate is only physically adsorbed by the support solid, and complete desorption of the chemisorbate from the solid support will occur upon said subsequent evacuation.

Moreover, chemisorption by the active phase in the first adsorption run, will effectively inactivate the reactive sites of the active phase such that the active phase will become chemically inert with respect to further contact with the chemisorbate subsequent to said evacuation.

Upon completion of the initial adsorption run, the chamber typically is quickly evacuated to desorb the desorbable chemisorbate. Pressure measurements need not be taken during evacuation, and the rate of evacuation is selected to be as fast as possible to save time. Upon completion of the evacuation, the adsorption mode is repeated, preferably immediately, for a second time typically at the same chamber temperature and mass flow rate employed for the initial adsorption run, and using the same chemisorbate. During the second adsorption run, however, only physical adsorption by the sample will occur, thereby resulting in the adsorption of less chemisorbate than occurred in the initial adsorption run. This amount is determined as a function of time, and the difference in the amount of chemisorbate adsorbed in the initial and second adsorption runs is determined over the same period of time. This difference is the amount of chemisorbate chemisorbed by the active phase.

The % dispersion of the active phase on the solid support can then be determined from the following equation:

$$\% \text{ Active Phase Dispersion} = (A/B) \times 100$$

wherein A is the number of atoms of chemisorbate chemisorbed by the active phase, and B is the number of atoms of active phase on the support solid. The value of A is determined from the differential amount described above and B is determined from the weight % of active phase on the support solid. In addition to the % active phase dispersion, the surface area of the active phase can also be determined by converting the amount of chemisorbate irreversibly chemisorbed to the corresponding number of molecules (atoms) of chemisorbate. The total surface area of the active phase is then determined from the known relationship between the number of chemisorbate molecules (atoms) chemisorbed per metal atom of the active phase and the area of each active phase metal atom.

The preferred embodiment of the apparatus used to conduct the methods of the present invention is described in connection with reference to the figures.

FIG. 1 is a block diagram of the preferred components of the Apparatus, namely, a gas supply section to serve as a source of the adsorbate or desorbate; a vacuum section capable of evacuating the chamber to a pressure of not greater than $10^{-5}$, preferably not greater than $10^{-7}$, and most preferably not greater than $10^{-9}$ mmHg; a flow controller section which contains a mass flow controller capable of controlling the mass flow rate of the gas being adsorbed or desorbed at a substantially constant value as described herein at the adsorbate and desorbate partial pressures also described herein; a pressure sensing and recording section capable of measuring and recording the pressure of the adsorbate or desorbate, typically with an accuracy of within about ±0.05 mmHg of the true pressure value; an adsorption or desorption section which includes a chamber capable of permitting introduction and withdrawal of the sample and the adsorbate or desorbate into or from a sample holder, as well as permitting control of the volume and temperature thereof as described herein; and an outgassing section which employs the vacuum section to assist in outgassing of the sample.

FIG. 2 illustrates the component parts of each section of the apparatus in a schematic diagram. More specifically, the gas supply section typically will contain one or more gas cylinders 101–104 which contain various different gases for adsorption or chemisorption. Each gas cylinder is connected to line 211 by conventional vacuum selenoid valves (ASCO TM) 7–10 respectively. These valves preferably are actuated in response to a signal from computer 117 at the appropriate time to permit gas to enter line 211. Line 211 is connected to the mass flow controller section via lines 200 and 201 through vacuum selenoid valve 3. During introduction of the gas into sample holder 109, vacuum selenoid valve 6 is closed and gas is passed from line 211 through open valve 3, through lines 200 and 201 and into the mass flow controller section.

The mass flow controller section of the apparatus contains a mass flow controller. A mass flow controller is an electronic device which operates on an adjustable aperature principle. The mass flow controller is preset to deliver gas to line 202 at a particular and substantially constant mass flow rate, e.g. the flow rate employed in the blank calibration run. However, due to the fact that gas passing through the mass flow controller is either being introduced or withdrawn from sample holder 109, a back pressure (during adsorption) or back vacuum (during desorption) develops in the sample holder which causes a decrease in the mass flow rate relative to the preset value. The mass flow controller continuously senses the actual flow rate with a flow meter, compares it to the preset value and compensates for any deviation from the preset value by opening or closing the aperature to increase or decrease the flow rate until the preset flow rate is again established.

In addition to fluctuations in the flow rate caused by variations in the pressure within the sample holder, there are other factors which must be controlled to achieve a substantially constant mass flow rate as described herein.

For example, to successfully employ a mass flow controller for the adsorption and chemisorption modes, the supply of the gas to the flow controller should be maintained at a substantially constant pressure, since mass flow controllers have been found to correct relatively slowly for changes or fluctuations in the incoming gas pressure. By substantially constant pressure is defined herein to mean deviations, if any, in the pressure of the incoming gas to the mass flow controller of typically not greater than about ±0.35, preferably not greater than about ±0.30, and most preferably not greater than about 35 0.20 psi. Pressure fluctuations are further reduced with the use of narrow tubing in the manifold as described herein. For the adsorption mode, the pressure of the adsorbate fed to the mass flow controller is typically controlled to be from about 16 to about 25, and preferably from about 16 to about 18 psig.

More importantly successful flow meters employed in conventional mass flow controllers typipcally operate on a principle wherein heat is transferred to or withdrawn from a flowing gas, and a temperature differential, induced at different points in the line of flow of the gas, by changes in the flow rate of the gas is employed to impart changes in the conductivity of a sensor proportional to the change in flow rate of the gas. It has been found that fluctuations in the temperature of the gas it enters the flow meter will cause error in the thermal sensing mechanism of such flow meters, particularly when operated under the conditions described herein on the order of about 1.5% of the mass flow rate for each °C. fluctuation in the adsorbate temperature. This error accumulates over extended periods of time to the extent that it significantly affects the accuracy of the flow rate sought to be determined. It has also been found that fluctuations in the temperature of the environment (e.g. room temperature) over extended periods of time, as employed for the adsorption and desorption modes described herein, also cause a relatively larger accumulated error in the mass flow rate relative to the preset value of the flow rate due to disturbances in the flow meter thermoresponsive sensing mechanism and the electronic circuitry of the flow controller. The combination of the aforedescribed errors precludes achieving substantially constant mass flow rates as described herein with conventional mass flow controllers under the entire range of conditions at which the methods of the present invention are conducted.

Accordingly, a mass flow controller which is capable of achieving substantially constant mass flow rates as described herein is disclosed and claimed in U.S. patent application Ser. No. 416,163, filed on an even date herewith, by the inventors herein, the disclosure of which is herein incorporated by reference.

Figure 4:
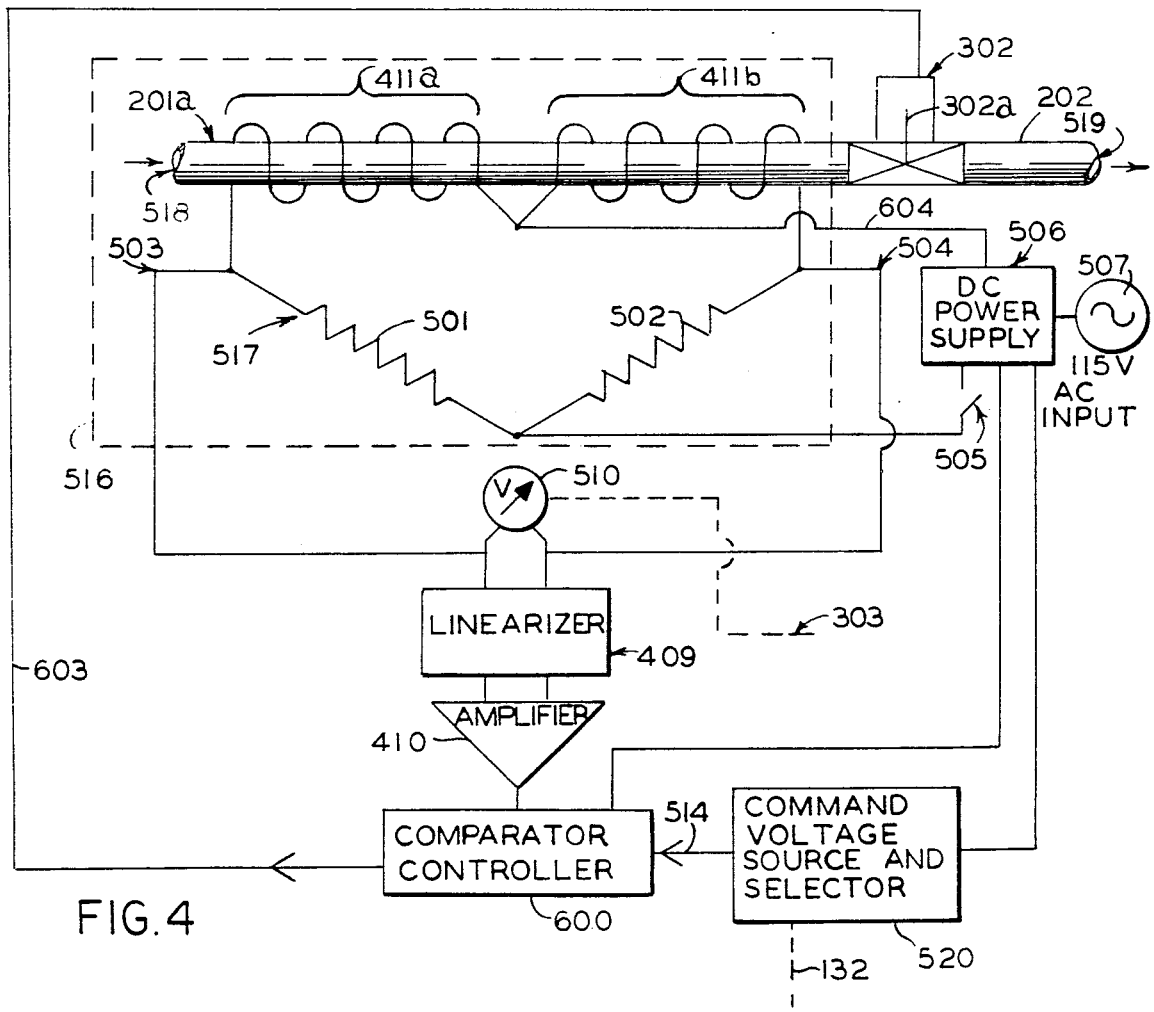
FIG. 4 is a more detailed schematic diagram of the mass flow controller circuit board 401 and flow regulating means within block 403 of FIG. 3.

A preferred embodiment of this mass flow controller is illustrated collectively in FIGS. 3 and 4. The integration of the mass flow controller 301 into the apparatus of the present invention is illustrated by FIG. 2.

Referring to FIG. 3, except for pressure controller 311, the components of the mass flow controller are housed in a temperature controlled box 119. This box encloses an inner space 608, which is in fluid communication with the atmosphere outside the box via vent 601 and hence is typically filled with air. The box is typically made of a sturdy material such as sheet metal and typically encloses a volume of about 2500 cc.

The temperature of the atmosphere within the box preferably is maintained above ambient room temperature to permit active control of the box temperature and thereby maintain such temperature constant. Typically, this temperature is maintained between about 35° and 45° C. (e.g. 39°C.) to avoid damaging the electronics housed within the box and to provide a sufficient temperature gradient between the atmosphere within and without the box that when room air from outside the box is drawn into the same by fan 407, a dynamic temperature equilibrium can be established within the box. Thus, the box temperature selected preferably will be above the temperature which the box would attain, absent a separate heat source, due to the heat given off by the electronics of the mass flow controller. Consequently, when air from the external environment of the box is mixed with air in the box and heated as described herein, the temperature equilibrium established within the box is not disturbed by the mass flow controller electronics.

Temperature control within the box is achieved by the combination of thermistor 404 which preferably is attached to the base of flow controller block 403, Proportional Integral and Derivative (hereinafter PID) Controller 405, heating strip 406, and fan 407. Thermistor 404 senses the air temperature within the box over a temperature range of 0° to 100° C. and generates an electrical signal proportional thereto which is sent to the PID controller. The PID controller (RFL model 70A) is preset to generate an electrical signal proportional to the difference between a preset box temperature and the actual box temperature. The PID generated electrical signal activates a heater strip 406 (e.g., of the resistive type 300 watt capacity). Thus, the strength of the electrical signal from the PID controller to the heater gets progressively weaker as the actual box temperature approaches the preset temperature and the signal is substantially constant when the actual box temperature equals the preset temperature to compensate for the heat loss to the environment. This provides extremely accurate temperature control. The fan 407 runs continuously during operation of the mass flow controller and circulates air in the box around the heating strip at a high rate of from about 10 to 100 (eg. 10-75) times the volume of the box per minute or higher. The fan 407 preferably is located close to vent 601 to draw fresh air into the box 119.

Controlling the temperature of box 119 performs at least four important functions, namely, (1) it heats incoming gas in line 201 so that by the time it reaches the flow meter sensing coil 411, it is at the same constant temperature as the box 119 irrespective of fluctuations in the room temperature; (2) it compensates for the temperature sensitivity of the electronic circuitry present in circuit board 401, thermal valve 302, and pressure transducer 108 (describe hereinafter); (3) it assures that the temperature of the gas in line 210 is constant at the point where measured by pressure transducer 108 and (4) it eliminates the effect of changes in ambient temperature on the gas within the chamber line volumes housed within the box 119 as depicted in FIG. 2, which changes would otherwise cause error in the measurement of the pressure of the gas within these lines. To assist box 119 in performing functions 1 and 3, line 201 is adapted to form coil 213 and line 210 is adapted to form coil 212. Coil volumes, (i.e. of the internal channel of the coil) of 0.5 cc for coil 213, and 0.8 cc for coil 212 are suitable to permit temperature equilibration of the gas in the coil to the box temperature.

The mass flow controller itself, is depicted as block 301 in FIG. 2. The input of mass flow controller 301 is connected to line 201, which contains pressure controller 311 (SERTA TM model 204) engaged in series therewith for maintaining the pressure of the gas entering the mass flow controller substantially constant, and the output to line 202. Mass flow controller 301 is illustrated in more detail in FIGS. 3 and 4. Referring to FIG. 3, the primary components of the mass flow controller include (a) stainless steel block 403 adapted to contain sensing conduit 201a which runs along the length thereof until it connects with thermal valve 302, sensing coil 411, and the controllable aperature portion of thermal valve 302 located downstream of sensing coil 411; (b) circuit board 401 which contains the electronic circuitry of the flow controller including, detector bridge circuit 408, linearizer 409, amplifier 410, and comparator controller 600; and (c) thermal valve 302. Pressure controller 311 is a necessary but auxiliary component of the mass flow controller.

Gas is introduced and withdrawn from sensing conduit 201a via conduit lines 201 and 202 respectively. Sensing conduit 201a starts at the entrance to block 403, passes through sensing coil 411 (which is shown as a single coil in FIG. 2, but is more specifically shown in FIG. 3 as two separate coils), and connects with the inlet portion of thermal valve 302. The outlet portion of thermal valve 302 is connected to line 202 by which gas then exits block 403. The body and electronic circuitry of thermal valve is seated on top of block 403 and encased in plastic housing 412.

The preferred thermal valve is available from Tylan Corporation and is described in detail in U.S. Pat. No. 3,650,505, the disclosure of which is herein incorporated by reference.

Circuit board 401 is encased in plastic housing 402.

The circuitry and operation of the mass flow controller is best described with reference to FIG. 4. Broken line 516 of FIG. 4 depicts the flow meter portion of the flow controller which contains bridge circuit 517 coupled to sensing conduit 201a. The bridge circuit is of conventional design and is formed of a first bridge resistor 501 and a second bridge resistor 502. The bridge circuit further comprises an upstream sensor element 411a and a downstream sensor element 411b. The sensor elements 411a and 411b are wound around the sensing conduit 201a adjacent each other with the upstream sensor element 411a closer to input end 518 of tube 201a and the downstream sensor element 411b closer to the output end 519 of conduit 202.

The bridge circuit 517 also comprises a D.C. power supply and converter 506, (which operates from AC power source 507) which is connected at one side via line 604 between the junction of the sensor elements 411a and 411b. The other side of the power supply is connected through a switch 505 to the junction of the bridge resistors 501 and 502. Output signals from the bridge circuit are coupled at a first output terminal 503 and a second output terminal 504. The first output terminal 503 is connected to the junction of the upstream sensor element 411a and first bridge resistor 501, and the second output terminal 504 is connected to the junction of the downstream sensor element 411b and the second bridge resistor 502. The upstream sensor element 411a and the downstream sensor element 411b are formed of temperature-sensitive resistance wire which is wound around the outer diameter of the conduit 201a. Such wire can be an iron-nickel alloy, e.g. Balco (a trademark of the Wilbur-Driver Company).

The above circuit design is conventional with the exception that the inner diameter of sensing conduit 201a is of capillary size of typically not greater than about 0.2, preferably not greater than 0.05 and most preferably not greater than about 0.02 mm and ranges from about 0.005 to about 0.2, preferably from about 0.01 about 0.1, and most preferably from about 0.01 to about 0.05 mm to achieve substantially constant flow rate. Furthermore, because of the low pressure and flow rates handled by the flow meter, a by-pass tube conventionally employed in mass flow meters should be avoided. It has been found that if the inner diameter of sensing conduit 201a is too large, the density of the gas within the tube becomes so low at the pressures and flow rates described herein that the thermal conductivity of the gas drops to the point where the thermal sensing mechanism (described hereinafter) of the flow meter is disrupted and substantially constant flow rate may not be attained.

The coupled bridge circuit output signals 503 and 504 are connected to linearizer 409 which electronically provides a linear output voltage as a function of mass flow. This voltage is applied through amplifier 410 to comparator controller 600. The linearizer, amplifier, and comparator controller are all conventional.

In operation, when the switch 505 is closed, current flows through sensor elements 411a and 411b causing the sensor elements to generate heat, thereby raising the temperature of the tube 201a adjacent the elements. Heating of elements 411a and 411b also raises their resistance. At zero fluid flow through the tube 201a, the temperatures of the sensor elements 411a and 411b are equal and the bridge is therefore balanced, producing a zero output voltage across the terminals 503 and 504. As fluid enters the input end 518 of the tube 201a, heat generated by the elements 411a and 411b is carried by the fluid downstream toward the output end 519 of the tube 291a. Thus, a temperature differential is created between the elements 411a and 411b due to the shifting temperature profile along the tube 201a. As the flow of fluid increases in the tube 201a, the temperature of the upstream element 411a as well as its resistance decreases while simultaneously the temperature of the downstream element 411b, as well as its resistance, increases. The bridge output voltage at terminals 503 and 504 therefor increases in nearly linear proportion to the flow rate. After linearization and amplification of the bridge output voltages of terminals 503 and 504, amplifier 410 applies a single linear voltage which corresponds to the absolute value of the mass flow rate of the gas before the gas reaches thermal valve 302. The voltage from amplifier 410 is applied to comparator controller 600 where it is compared to an external electrical command signal 514 from command signal source and selector 520 which has been preset to correspond to a selected mass flow rate. The comparator controller establishes the difference, if any, between the command signal voltage and the amplifier voltage and utilizes it to power the actuator 302a of thermal valve 302 via line 603. The thermal valve actuator is thus controlled so that it opens more when the comparator control indicates that the mass flow rate is insufficient to balance the command signal, and is closed more when the opposite situation occurs.

When the command signal is selected using selector 520, the latter also sends a digital signal via line 132 to computer 117 of FIG. 2, representative of the flow rate which has been selected and which has previously been calibrated with a blank run.

In a more preferred alternative embodiment sensor elements 411a and 411b can be combined into a single coil containing a center tap as illustrated in U.S. Pat. No. 3,938,384, the disclosure of which is herein incorporated by reference. By utilizing a single coil with a center tap rather than two separate sensor elements, it is possible to space the coils close together. Thus, heat loss is reduced, equalization between the upstream and downstream sensor elements is facilitated, and the gain of the circuit (temperature change per unit of flow) is greater. In addition, the response of the circuit is faster, and the range of useful flow measurement and the linearity of the circuit is increased.

An optional feature of the circuit illustrated in FIG. 4 is volt meter 510 connected across the coupled output terminals 503 and 504. The electrical signal from the volt meter is converted from an analog signal to a digital BCD signal by a converter (not shown) and the BCD signal is sent to computer 117 of FIG. 2 via line 303. During the blank calibration run, the computer samples the output from volt meter 510 over a period of about 10 minutes, during which period it acquires data at a rate of about 1 data point per second and averages the acquired data which is stored in a data base as a calibrated value. During an adsorption or desorption run, the computer compares the calibrated value with the actual value sampled from the volt meter during the ad- or desorption run in order to determine if the run is carried out reliably. This is a quality control feature which permits observation of any deviations from the desired flow rate after completion of the run.

It is to be understood, that while the mass flow controller has been described with respect to a particular flow meter, other types of flow meters can be used which provide an electrical signal v.s flow function, such as described in U.S. Pat. Nos. 3,650,151; 4,056,975; 4,100,801 and the like. While a thermal valve as described herein is preferred to regulate the flow rate, any other electrically actuated means which possesses the sensitivity and capability of regulating the flow rate to be substantially constant at the conditions of use described herein can be employed. Similar considerations also apply with respect to the mass flow controller itself. The present invention requires the capability of achieving a substantially constant flow rate throughout the range of conditions of low flow rates and low pressures, over extended periods of time described herein. While it is believed that the inventors herein are the first to develop devices with such capabilities, the method and apparatus of the present invention does not preclude the use of alternative means which perform the necessary functions of the mass flow controller and associated environmental control box should they be developed.

Returning to FIG. 2, gas passing through line 201 located within environmental control box 119, passes through coil 213 wherein its temperature equilibrates with the temperature of said box 119, passes through flow controller 301, wherein its rate is regulated as described herein and enters the sample holder 109 of the sample holder section via lines 208, 209, vacuum selenoid valves 4, and 5, and stopcock 19.

The sample holder section comprises sample holder 109, liquid bath container 111, liquid level controller 113 +20, and liquid bath 112. Sample holder 109 typically is a glass flask of about 20 ml in volume having a glass capillary neck 122 about 2 mm inner diameter. The capillary neck terminates with a ground glass joint 123 adapted to receive male ground glass joint 124 of line 125. To add or remove sample 110 to or from sample holder 109, ground glass joints 123 and 124 are disconnected. The assembly (referred to herein as Assembly A) comprising ground glass joint 124, line 125, which is connected to stopcock 19, which is connected to line 126 and its associated ground glass joint 127, is used for sealing and/or connecting sample holder 109 to either the outgassing section, e.g., at ground glass joint 21, or to the mass flow controller section at the end of line 209 using ground glass joint 128, e.g., Assembly A permits sealing a sample holder that contains a sample by closing stopcock 19 after outgassing and evacuation. Thus, Assembly A and sample holder 109 permit sealing and transfer of sample holder 109 to the desired location in the apparatus.

Liquid bath container 111 typically is a dewar flask capable of holding the liquid bath, such as liquid nitrogen, and larger enough to accept immersion of sample holder 119 therein when it is connected to the mass flow controller section. As described above, the liquid bath 112 is typically liquid adsorbate or desorbate, and when the level 129 of the bath 112 is maintained constant in liquid bath container 111 during ad- or desorption, the bath 112, serves to control the temperature of sample holder 109 when immersed therein. The level 129 of bath 112 in relation to the depth of immersion of sample holder 109 also dictates the volume of the sample holder $V_{S.H.}$ in equations 1, 2 and 3 while the bath 112 temperature sets the temperatures $T_{S.H.}$ and/or $T'_{S.H.}$ in the same equations. For example, container 111 is filled with sufficient bath 112 so that the bath level 129 in container 112 intersects the capillary neck 122 of sample holder 109 at point 130 on said capillary neck 122. The location of point 130 typically is midway between ground glass joint 123 and the termination of the capillary neck of sample holder 109 at point 132. Sample holder rack 131 is set within container 111 to stabilize the sample holder and assure that the sample holder 109 is immersed to the same depth within bath 112 for each run when the bath level 129 is constant. Thus, $V_{S.H.}$ is the volume of sample holder 109 which is immersed in bath 112, i.e. the volume of capillary neck from point 130 to 132+ the volume of the remaining noncapillary volume of sample holder 109.

The level 129 of bath 112 in container 111 is held constant with a conventional liquid level controller such as a Hungtington Electronics Inc Model 200, collectively depicted as bath level sensor 113 and control valve 20 actuated by sensor 1134 adapted for use herein. For Example, when employing liquid nitrogen as the liquid bath, the liquid nitrogen tends to evaporate during the course of the experiment. Consequently, additional liquid nitrogen must be added to maintain the bath level substantially constant. Accordingly, bath level sensor 113 senses a change in the bath level and activates control valve 20 to allow fresh liquid to enter lines 308 and 310. However, as liquid nitrogen enters lines 308 and 310, the temperature of the lines is warmer than the liquid nitrogen thereby causing the nitrogen to evaporate explosively. Liquid and vaporized nitrogen would therefore ordinarily be violently discharged into the liquid bath 112 thereby upsetting the bath level 129. This causes error in the pressure recorded as a function of time. It has been found that this problem can be eliminated quite effectively by installing a vent line 309 which effects separation of the fresh bath vapor from the fresh bath liquid before the fresh bath liquid enters the liquid bath container. This procedure maintains the bath level substantially constant within a deviation of about ±0.5 mm. Thus, a liquid bath 112 evaporates, control valve 20 receives fresh liquid from line 307 which is connected to a source of the liquid bath (not shown). Bath liquid passes from control valve 20, through line 308 and into line 310, the open end of which is immersed in the liquid bath 112. Line 309 is a vent open to the atmosphere and in fluid communication with lines 308 and 310. The end of line 310 has a glass wool plug inserted therein to create a backpressure and cause any vaporized liquid bath to exit via vent line 309 rather than be discharged violently into liquid bath 112. This avoids upsetting bath level 129 and is a way to maintain the bath level substantially constant. By maintaining bath level 129 substantially constant, the volume $V_{S.H.}$ at temperatures $T_{S.H.}$ is also held substantially constant.

Accordingly, by the combined use of box 119 to control the temperature of the chamber line volume, and the liquid bath to control the temperature of the sample holder volume, the total chamber volume, and the gas contained therein is maintained at a substantially constant temperature. By substantially constant temperature as applied to the total chamber volume is meant deviations, if any, in the average temperature of the total chamber volume of typically not greater than ±0.35, preferably not greater than ±0.20 and most preferably not greater than 0.17% of said average temperature value.

The primary components of the pressure sensing and recording section of the apparatus comprise pressure transducer 108 (SETRA ™ 204 300A) and a pressure recording device such as computer 117 (Apple II ™) and/or strip recorder 118. Pressure transducer 108 is located in environmental control box 119 and the input end thereof is connected to line 208 (located between vacuum selenoid valves 4 and 5) by line 210 and coil 212, said coil 212 also being located within environmental control box 119. Line 208 is in fluid communication with the sample holder during both adsorption and desorption. Within coil 212 the gas in line 210 is heated to the equilibrium temperature of box 119. Thus, some of the gas flowing in line 208 passes through line 210 and coil 212 and contacts the input end of pressure transducer 108. The temperature of the gas in coil 212, i.e. the box temperature, is therefore constant, and changes in pressure in line 210 reliably reflect changes in pressure in the sample holder 109. The pressure transducer 108 senses the pressure in line 210 at constant temperature, and converts the pressure to an electrical signal which is passed from the output end of pressure transducer 108 to the input end of interactive structures A/D model A 003-4 converter 121 via line 304. Converter 121 changes the analog electrical signal from pressure transducer 108 to a digital electrical signal. This digital signal is passed from the output end of converter 121 to digital computer 117 via line 306.

Optionally, the output analog electrical signal from pressure transducer 108 can be passed to strip recorded 118 via line 305.

Computer 117 and strip recorded 118 are alternative means for recording the pressure of the gas being introduced or withdrawn from sample holder 109 as a function of time and can be used alone or in combination. However, the use of a computer is preferred.

Accordingly, for the adsorption mode, the computer 117 is programmed to enable it to: (a) record, typically on a semicontinuous basis, digital pressure signals received indirectly from pressure transducer 108 as a function of time to establish and store a first data base of pressure vs. time; (b) establish and store a second data base of several different mass flow rates, one of which is selected by the computer operator; (c) convert the pressure vs. time information in the first data base and the selected mass flow rate in the second data base to a third data base of all or part of the adsorption isotherm, i.e. $V_{ads}$ v. $(P/P_s)$ and store the 3rd data base; and (d) calculate the surface area of a sample using, for example, the BET equation from the information in the 3rd data base.

For the desorption mode, computer 117 is programmed to establish and store the first and second data bases described above in connection with the adsorption mode, during operation of the desorption mode. The computer then establishes and stores a 3rd data base of the desorption isotherm, i.e., $V_{dsb}$ v. $(P/P_s)$ and uses the 3rd data base to calculate the pore size distribution of the sample using, for example, the Kelvin equation, and the total pore volume using Equation 11.

To establish the first data base described above of pressure vs. time, the computer samples and stores digital pressure signals during an ad-or desorption run on a semicontinuous basis. The frequency of sampling is controlled by the operator. The particular frequency selected is described herein.

To establish the second data base of mass flow rates described above, the command voltage source and selector 520 is calibrated at about 12 different voltage settings using blank runs and the actual mass flow rate for each blank run is determined. The 12 flow rates employed typically will vary from about 0.2 to about 0.7 ml/min at S.T.P. The computer is then programmed with these calibrated flow rates, and a digital voltage associated with each command voltage.

Consequently, when the operator selects one of the calibrated command voltage settings for a run, the command voltage selector 520 automatically sends the corresponding digital signal to the computer 117 via line 132 representative of the selected flow rate. The computer 117 uses this information to determine what mass flow rate should be employed to calculate the amount of gas ad-or desorbed as described herein. The ability of a computer to automatically perform the aforenoted operations is another advantage of, and made possible by, the use of a substantially constant mass flow rate.

The computer also performs several additional functions which serve to automate the system completely.

Thus, the computer manipulates many of the functional components of the apparatus, including: opening and closing selenoid valves for: selection of gas from the gas supply section; introduction or withdrawal of gas from the sample holder 109; evacuation of sample holder during outgassing; and saturation of the sample with condensed gas preparatory to a desorption run. The computer also controls outgassing conditions, such as temperature and duration.

The vacuum section supplies the vacuum to outgas the sample, evacuate the sample holder, and desorb the desorbate from the desorbent. The vacuum section comprises a mechanical and a diffusion vacuum pump collectively shown and referred to as vacuum pump 105, and pressure gauge 120 (Edward CP25 Gaugehead). The mechanical pump (Varian 0401-K6820-301) reduces the pressure in line 204 to $10^{-3}$ mm Hg, while the diffusion pump (Varian 0160-82906-301) disposed in series with the mechanical pump, reduces the pressure to the desired level of $10^{-7}$ to $10^{-8}$ mm Hg.

The pressure gauge 120 reads the pressure directly from line 204 as a check on the proper functioning of the vacuum pumps. The vacuum end of vacuum pump 105 is connected to the apparatus via line 204 which connects with lines 205 and 203. By appropriately opening and closing vacuum selenoid valves 1 and 2, the outgassing and adsorption/desorption sections can alternately be engaged with vacuum pump 105.

The outgassing section comprises aluminum heating block 14, one or more conventional cartridge heaters 115, vacuum selenoid needle valve 11, and A.C. power source 16 to supply current to the cartridge heaters. The aluminum block is milled to provide a space 114 adapted to accommodate sample holder 109'. While only one space 114 and one sample holder 109' is shown, aluminum block 14 typically is adapted to receive and heat 4 sample holders. Assembly A, comprising ground glass joint 127', capillary line 126', stopcock 19', capillary line 125' and ground glass joint 124' permit interfacing the sample holder 109' with the vacuum section via ground glass joint 21, electrically operated vacuum selenoid 11 and line 206. To add a sample to sample holder 109', Assembly A is disconnected, the sample 110', added to the sample holder 109', and Assembly A reconnected, as shown.

To outgas the sample the vacuum pump 105 is started, stopcock 19' is opened, selenoid valve 1 is closed, vacuum selenoid valve 2 is opened, and vacuum selenoid valve 11 is initially opened intermittently to avoid sucking sample 110' out of the sample holder. The cartridge heaters are engaged and the sample heated under vacuum until outgassing is completed. Stopcock 19' is then closed while the sample holder is still under vacuum to maintain the sample 110' in the evacuated state while being transferred to the adsorption/desorption section. Selenoid needle valve 11 is then closed, and Assembly A while connected to sample holder 109', is disconnected from ground glass joint 21. The sample holder-Assembly A combination is allowed to cool and then connected to the adsorption/desorption section as discussed.

All gas conduit lines illustrated in FIG. 2 are constructed of 0.05 to 0.2 inch I.D. stainless steel tubing up to metal glass connectors 135 and 136. All glass gas conduit lines are capillary lines of about 2–6 mm inner diameter and 7–12 mm outer diameter. All selenoid valves are conventional electrically actuated vacuum valves (Hardman-VA-250-AE1-2-10-21) with the exception of valve 1 which is an air operated valve (ASCO TM) and valve 11 which is an electrically operated needle valve (Whitey TM). Valves 4 and 2 are put in backwards because they work in only one direction. If pressure is applied to the low pressure side of these valves, they act as a check-valve. All metal joints are welded where possible.

For the adsorption mode, line volumes constituting $V_L$ in equations 1, 2 and 3 which must be known are those defined between valve 302 and point 130 on line 122, including lines 202, 208, 209, 126, 125, and 122 as well as lines 210 and coil 212.

For the desorption mode, valve 4 will be closed and the circuit of line volumes starting from valve 302 constituting $V_L$ in equations 1, 2 and 3 which must be known are coil 213, lines 201, 207, 208, 209, 126, 125, and 122 up to point 130 on line 122, as well as line 210 and coil 212.

Representative volumes include: from valve 19 up to and including sample holder 109 about 20 ml; from valve 19 to mass flow controller 301 about 19 ml; from exit of box 119 in line 209 to point 130 on line 122 about 0.6 to 0.8 ml; lines 201 and 207 including coil 213 about 4 ml; and in line 210 and coil 212 about 7.5 ml. Thus from FIG. 2 it can be seen that by locating lines 201, 202, 208, 210 and 207 within box 119, only a very small fraction of the line volume critical to pressure measurements is exposed to room temperatures and associated fluctuations therein. The effect of such fluctuations is therefore minimized to the extent that they can be ignored. Accordingly, it is preferred to maintain from about 94 to about 99, and preferably from about 96 to about 98% of the chamber line volume, within box 119, excluding any chamber line volume below bath level 129.

At the start of the adsorption run, outgassing has been completed, valve 2 is closed, and evacuated sample holder 109 and Assembly A are connected to ground glass joint 128 with stopcock 19 closed. The sample holder 109 is therefore appropriately situated in the liquid bath. Valves 1, 4, 5 and 6 are then opened and vacuum pump 105 started to evacuate the system. After about 5 minutes, evacuation is completed, and stopcock 19 is opened while valves 5 and 6 are closed. Valve 3 and one of valves 7 to 10 are then opened to stabilize the mass flow controller which takes about 5 minutes. The appropriate command voltage is selected, valve 1 is then closed and valve 5 opened at the same time. Adsorbate flows into the sample holder from line 211 tracing an input path defined by the open and shut valves described at this point, and the pressure will start to rise. Appropriate measurements of pressure vs. time are made and the surface area of the sample is taken.

To conduct the desorption mode, the outgassed sample containing sample holder 109 is in place as described at the start of the adsorption mode. Valve 2 remains closed during the entire operation. The system is evacuated by opening valves 1, 4, 5, and 6. Stopcock 19 is then opened. The sample is then saturated with desorbate by closing valves 1 and 6 and opening valve 3 and one of valves 7 to 10 to select the appropriate adsorbate. Valves 4 and 5 remain open during saturation. The mass flow rate can be initially high since pressure readings are not taken during saturation when only the desorption mode is to be conducted. Saturation generally will take a long time, e.g. about 1 to about 8 hrs. because all of the pores of the sample must be filled with liquid desorbate. However, as a matter of convenience, care should be taken not to oversaturate the sample to the extent that desorbate condenses on the sample holder 109 wall. Such an occurance will unnecessarily prolong the desorption mode duration. When the sample is saturated, the desorption mode can start. Desorption is initiated by closing valves 3 and 4 and opening valves 1 and 6, valve 5 remaining open. The configuration of opened and closed valves is necessitated by the fact that the mass flow controller operates in only one direction. Consequently the vacuum section must pull the desorbate through the mass controller in its forward operating direction. If the sample is properly saturated, the desorbate pressure will remain constant for several minutes. For calibration calculations, t=0 at the moment the pressure starts dropping. It is at this moment that any and all of the condensed desorbate on the sample holder wall and in between the sample particles is removed. Pressure sensing and recording, however, is initiated at the same time as desorption.

To conduct combined adsorption and desorption modes, the adsorption mode is employed to saturate the sample and pressure vs. time readings are taken during both adsorption and desorption.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In all of the following examples the apparatus in its preferred embodiment as described in connection with the description of FIGS. 2, 3, and 4 was employed.

EXAMPLE 1

Figure 5:
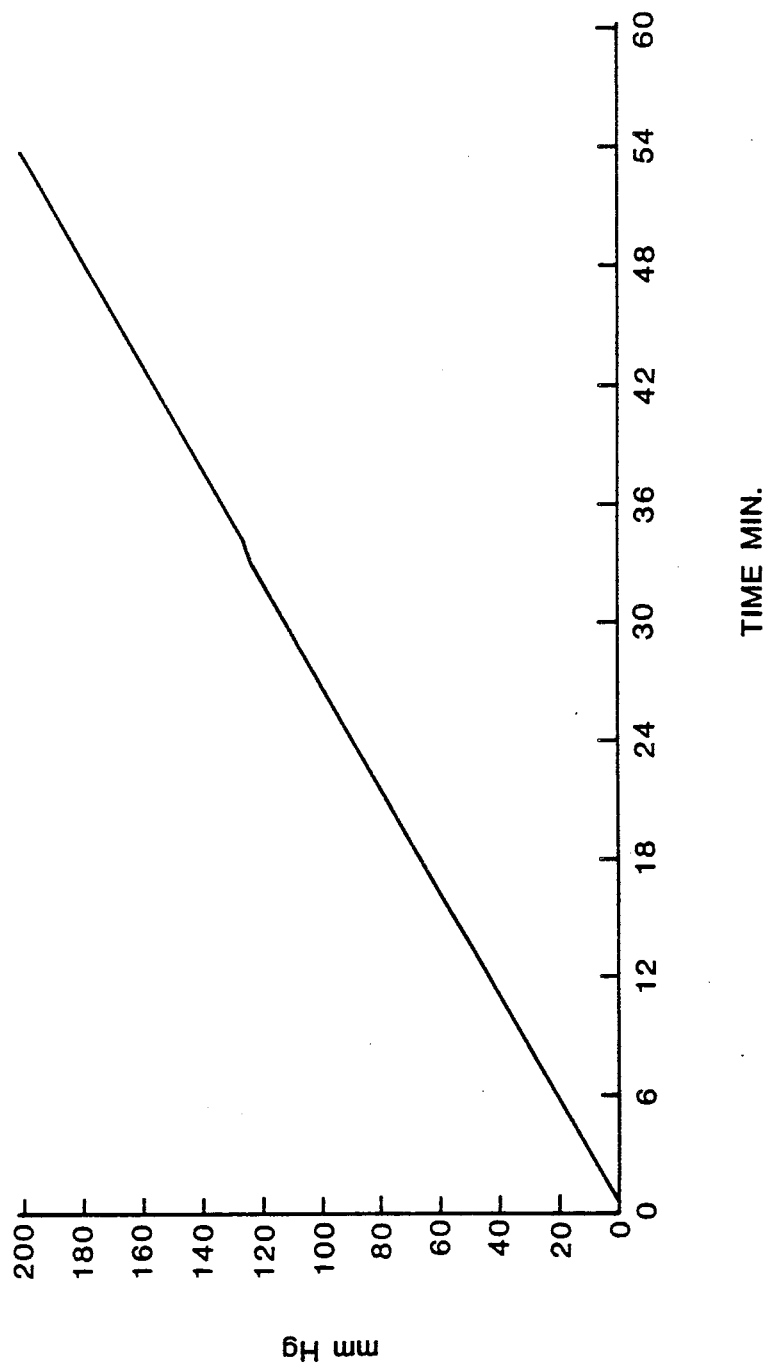
FIG. 5 is a pressure vs. time plot of an adsorption blank calibration run generated in accordance with Example 1.

This example illustrates a blank calibration run for the adsorption mode repeated 3 successive times and the individual plots overlaid on each other in FIG. 5. The following Table 1 lists the appropriate parameters employed.

TABLE 1

| | |
|---|---|
| Adsorbate | $N_2$ |
| Saturation Pressure | 760 mm Hg |

TABLE 1-continued

| | |
|---|---|
| Chamber Line Vol. ($V_L$) | 20.01 cc. |
| Sample holder vol. ($V_{S.H.}$) | 21.60 cc. |
| Liq. $N_2$ bath Temp. ($T_{S.H.}$) | 77.2° K. |
| Line Temp. ($T_L$) | 296.0° K. |
| Partial Pressure Range | 0 to 0.263 |
| No. of Pressure/time data points sampled | 1,260 |

The run is conducted as described for the adsorption mode. The flow rate was calculated from equation 1 to be 0.5 ml/min at STP. Plots of the pressure vs. time generated by a Hewlett Packard 7225A plotter hooked up to the computer are provided at FIG. 5. As may be seen therefrom a straight line results representative of a substantially constant mass flow rate. The degree of scattering of data points is calculated by (1) determining the absolute value of the deviation of the pressure value for each data point from the pressure valve that corresponds with the best straight line through all the data points; (2) averaging the absolute values of the deviation; (3) relating this average to the pressure in the system and expressing this value as a percentage.

The degree of scattering is a way of expressing the constancy of the flow rate. For this example, the degree of scattering for all three plots was 0.8%.

EXAMPLE 2

This example illustrates a blank calibration run for the desorption mode. The following Table 2 is lists of the appropriate parameters employed:

TABLE 2

| | |
|---|---|
| Desorbate | $N_2$ |
| Saturation Pressure | 760 mm Hg |
| Chamber Line Vol. ($V_L$) | 36.68 cc. |
| Sample holder vol. ($V_{S.H.}$) | 21.60 cc. |
| Liq. $N_2$ bath Temp. ($T_{S.H.}$) | 77.2° K. |
| Partial Pressure range ($P/P_s$) | 1.0 to 0 |
| Line temp. ($T_L$) | 296° K. |
| No. of pressure/time data points sampled: | 30,000 |

Figure 6:
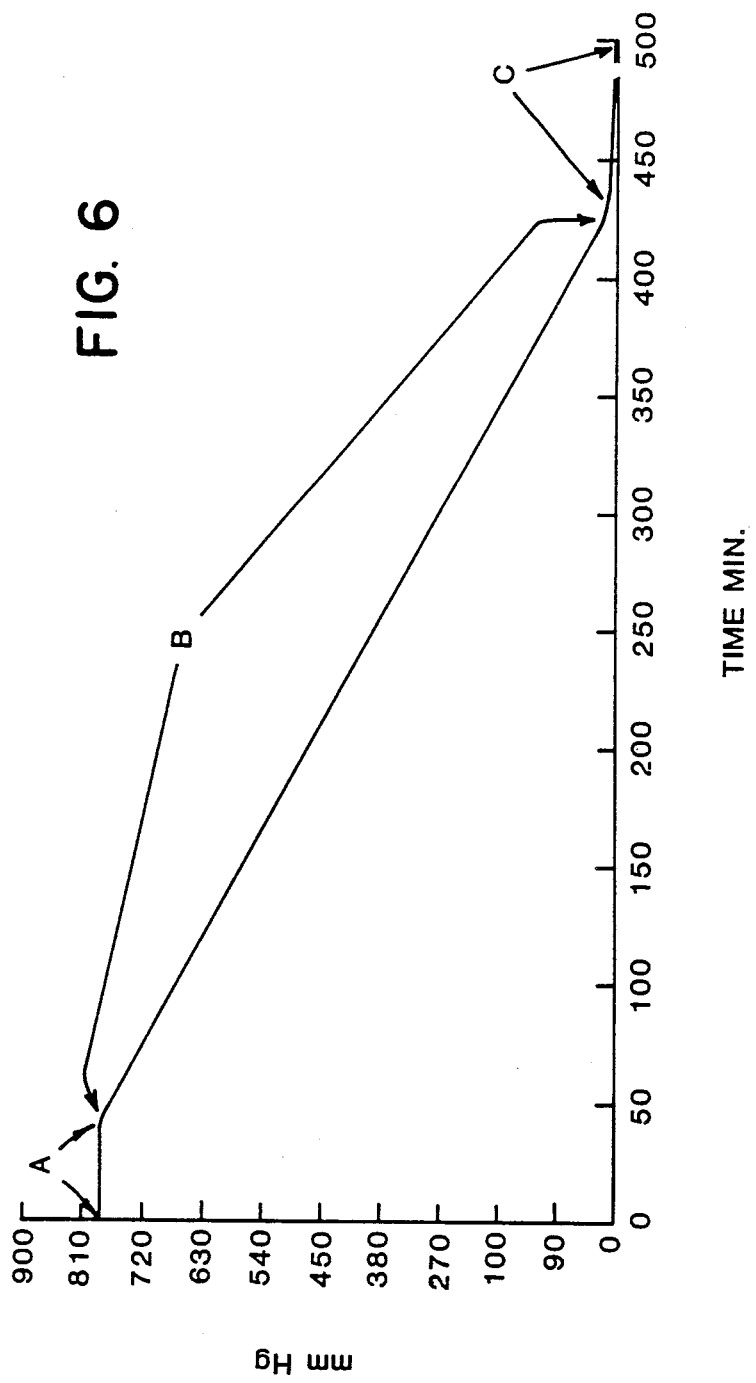
FIG. 6 is a pressure vs. time plot of a desorption blank calibration run generated in accordance with Example 2.

The mass flow rate was calculated to be 0.30 ml/min with a degree of scattering of 0.24%. A plot of pressure vs. time generated by the computer and plotter is provided as FIG. 6. As may be seen therefrom the plot is divided into 3 segments A, B, and C. Segment A represents the constant pressure caused by evaporation of condensed desorbate within the sample holder. At the end of segment A all condensed desorbate has been removed and the plot abruptly shifts slope which remains substantially constant throughout segment B. Thus, segment B represents withdrawal of desorbate at a substantially constant rate.

At the end of segment B and at pressures near absolute vacuum the slope again shifts. It is at this point when the mass flow controller is unable to maintain the flow substantially constant. However, this does not occur until a partial pressure ($P/P_s$) of about 0.02 is reached. This partial pressure is well below that needed to obtain enough of the desorption isotherm to calculate the pore size distribution of the sample and provide a substantially complete desorption isotherm.

EXAMPLE 3

This Example illustrates an actual adsorption run. The sample chosen for the surface area determination is a silica-alumina ASTM Standard No. N10074 having a reported surface area of between 281 to 297 m²/g depending on the method used for the determination. A previously calibrated blank was employed to determine the mass flow rate. The sample was outgassed in the sample holder under vacuum at 400° C. for 700 min. The appropriate parameters of the adsorption run of this Example are summarized below in Table 3.

TABLE 3

| | |
|---|---|
| Adsorbate | $N_2$ |
| Sample type | Silica-alumina |
| Sample weight | 1.074 (g) |
| Sample density | 3.2 (g/cc) |
| Saturation pressure | 760.00 (mm Hg) |
| Chamber line vol. ($V_L$) | 20.01 cc |
| Sample holder vol. ($V_{S.H.}$) | 21.60 cc |
| Liq. $N_2$ bath Temp. ($T_{S.H.}$) | 77.2 (°K.) |
| Line temp. ($T_L$) | 315 (°K.) |
| Mass flow rate | 0.30 (ml/min) |
| Partial pressure range | 0 to 0.263 |
| Total no. of pressure/time data points sampled | 25,440 |

Figure 7:
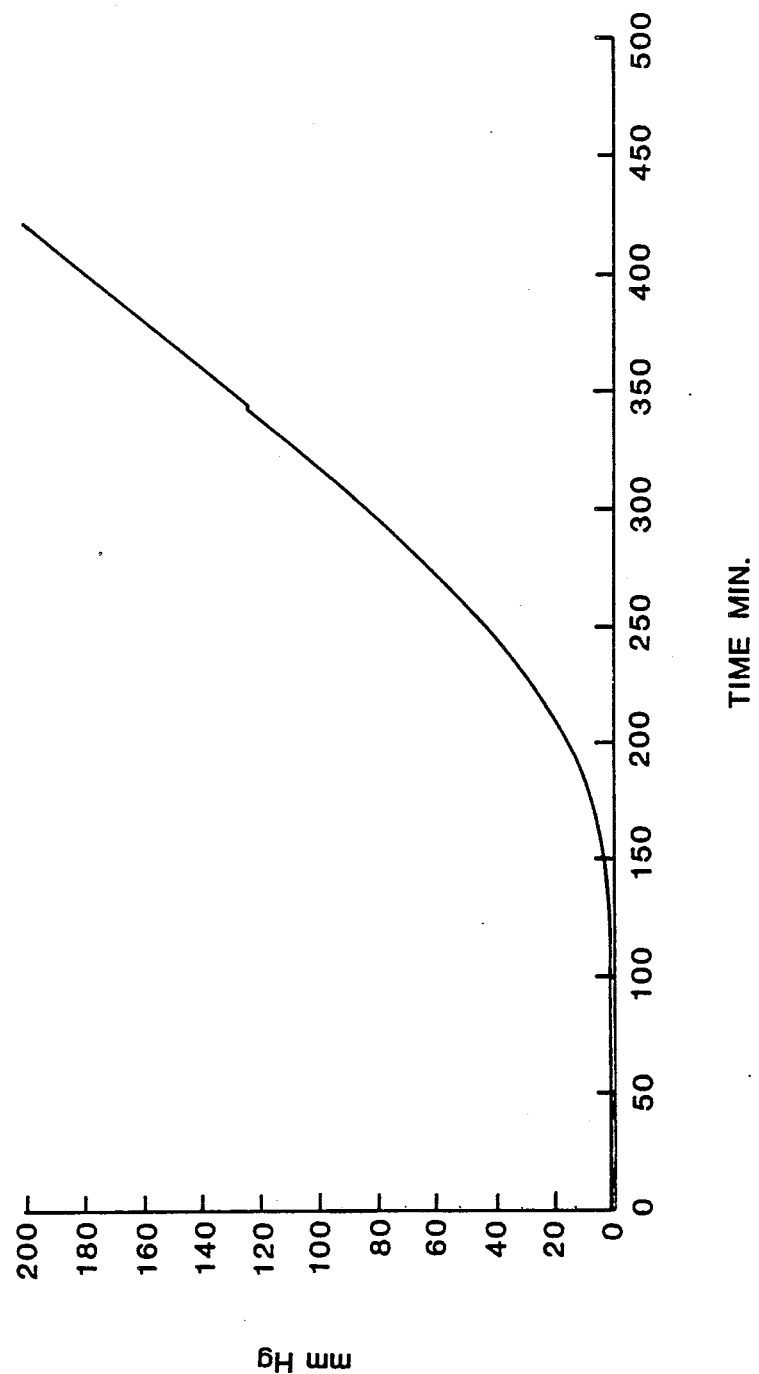
FIG. 7 is a pressure vs. time plot of an adsorption mode run generated in accordance with Example 3.

Of the total pressure/time data points sampled by the computer, 10 approximately equidistant sampled chamber pressure points on the plot are reported herein for convenience at Table 4. The actual plot is shown at FIG. 7. The reference pressures corresponding to the reported sampled chamber pressure are also directly shown at Table 4. The volume of adsorbate at STP adsorbed per gram of sample, as well as the relative adsorbate pressure ($P/P_s$) at which this amount is adsorbed, is calculated from the difference between the CRP and SCP using equation 2 and the entire pressure time data base.

TABLE 4

| Data Point No. | CRP (mm Hg) | SCP. (mm Hg) | V | (X) Pr | (Y) $\frac{Pr}{V(1-Pr)}$ |
|---|---|---|---|---|---|
| 1 | 311.0 | 2.810 | 35.818 | 0.004 | 0.000 |
| 2 | 378.0 | 6.840 | 43.151 | 0.009 | 0.000 |
| 3 | 445.0 | 15.630 | 49.954 | 0.021 | 0.000 |
| 4 | 511.0 | 30.300 | 55.989 | 0.040 | 0.001 |
| 5 | 578.0 | 50.390 | 61.545 | 0.066 | 0.001 |
| 6 | 645.0 | 74.150 | 66.704 | 0.098 | 0.002 |
| 7 | 712.0 | 101.00 | 71.531 | 0.133 | 0.002 |
| 8 | 779.0 | 128.00 | 76.354 | 0.168 | 0.003 |
| 9 | 845.0 | 157.00 | 80.852 | 0.207 | 0.003 |
| 10 | 912.0 | 187.00 | 85.368 | 0.246 | 0.004 |

CRP = Chamber reference pressure, extrapolated beyond 600 mm Hg
SCP = Sampled chamber pressure
V = Volume of adsorbate adsorbed per gram of sample at STP (cm³)
Pr = Relative pressure The linearized version of the BET equation is plotted from Relative Pressure (x-axis) and as the y-axis the value calculated for:

$$Pr/[V(1-Pr)]$$

at each relative pressure. The slope, and y-intercept of the plot were calculated to be 0.000 and 0.015 respectively. The surface area was then determined to be 284.2 m²/g.

EXAMPLE 4

Figure 8:
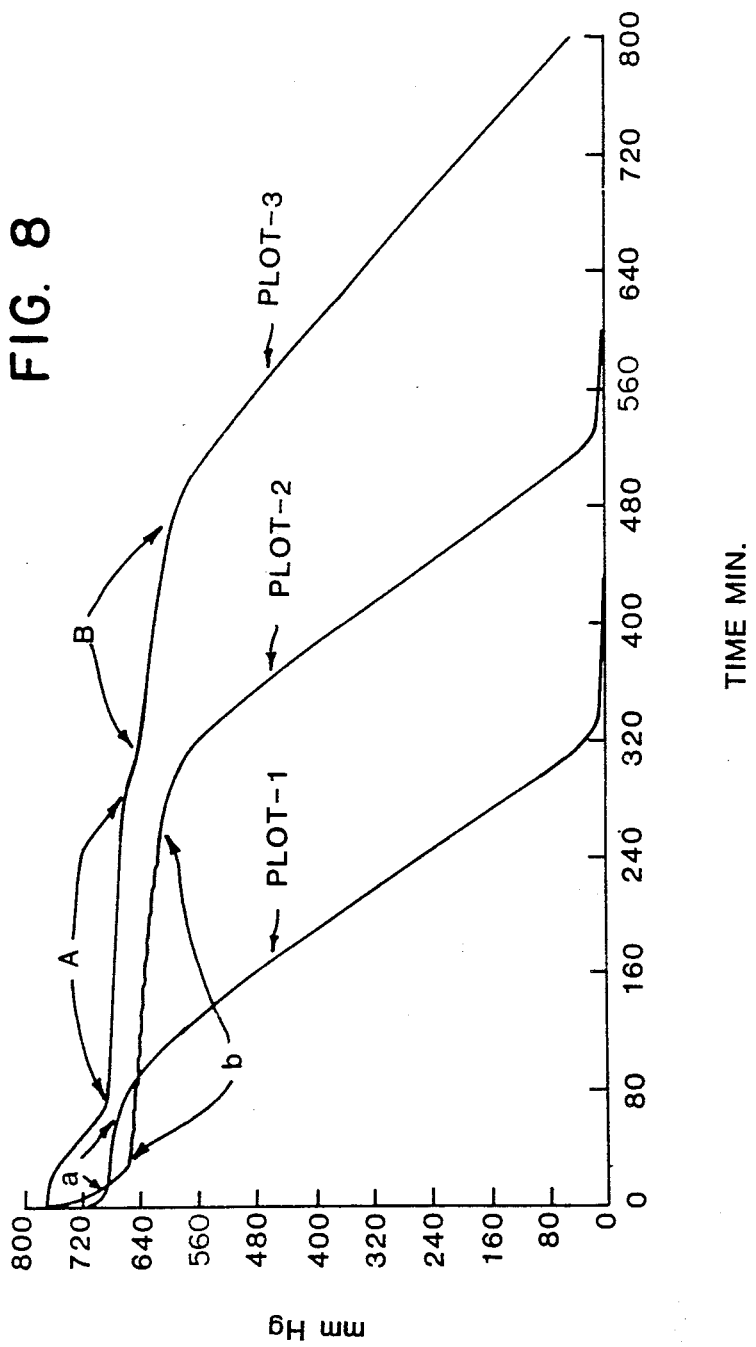
FIG. 8 is a collection of 3 pressure vs. time plots of a desorption mode run generated in accordance with Example 4.
Figure 9:
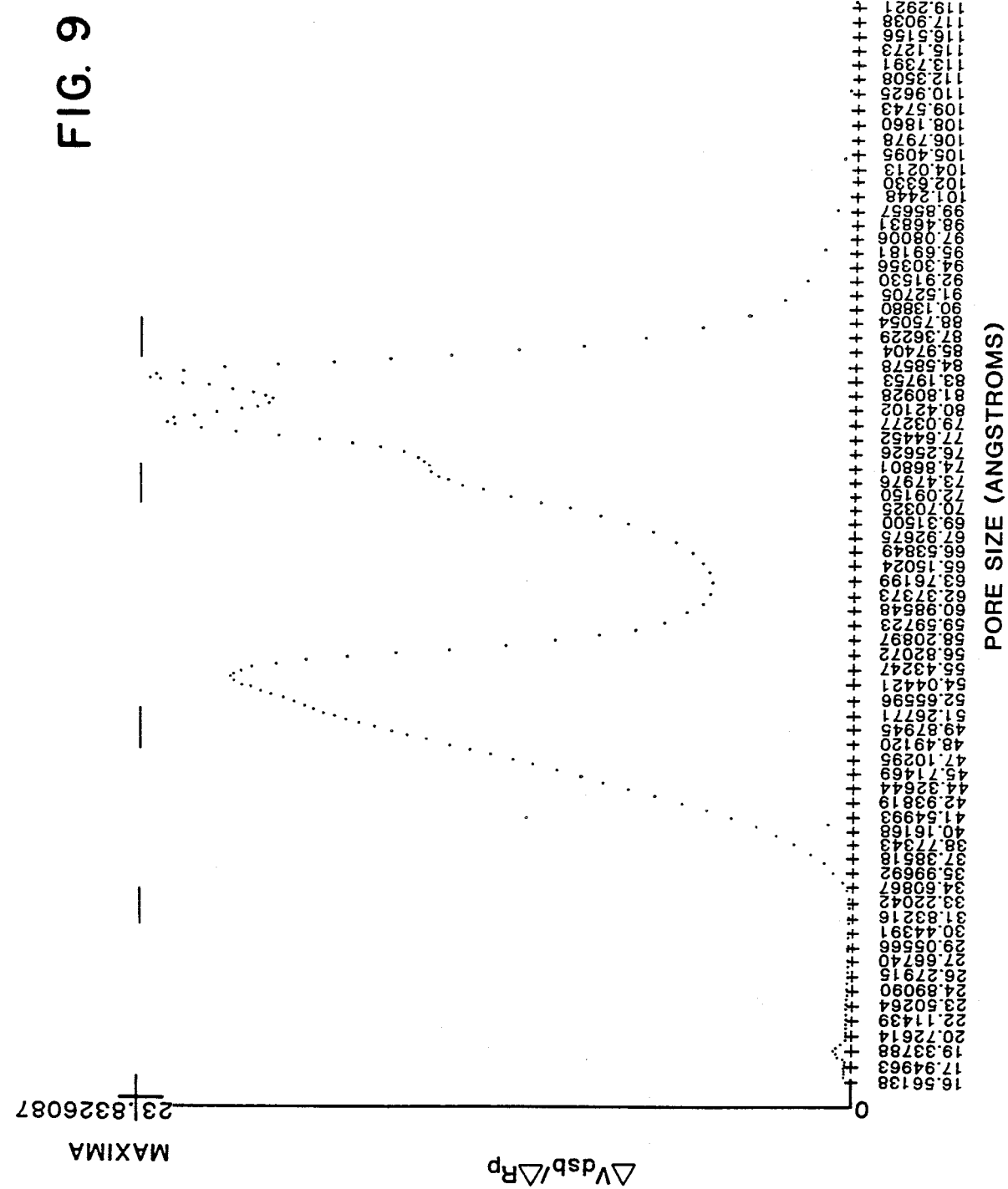
FIG. 9 is a pore size distribution plot generated in accordance with Example 4.

This example illustrates the desorption mode and employs 3 different runs. In the first run a sample of pore glass Sample A, was subjected to the desorption mode. In Run 2, a different sample of pore glass was used, i.e. Sample B. In run 3, a 50 wt. % ratio mixture of pore glass samples A and B respectively was employed. Each sample was outgassed under vacuum at 375° C.

for 700 min. Each sample was then saturated with N₂ desorbate until a sample saturation pressure as reported in Table 5 was attained in the sample holder. Desorption was then commenced at the mass flow rate reported in Table 5. The computer samples the decrease in pressure as a function of time at a frequency of about 60 data points per minute and plots pressure vs. time as provided in FIG. 8. In FIG. 8, plot 1 corresponds to Sample A, plot 2 to Sample B, and plot 3 to the mixture of samples A and B. Plot 3 illustrates the high degree of resolution, obtainable from the method and apparatus of the present invention, between the pressure/time profile attributable to sample A and that attributable to sample B. More specifically, segment A of plot 3 corresponds to segment a of plot 1 and segment B of plot 3 corresponds to segment b of plot 2. The extent of this resolution is more clearly seen, however, from the pore size distribution plot of $\Delta V_{dsb}/\Delta R_p$ as provided in FIG. 9 from the data of plot 3. As may be seen from FIG. 9 the pore radius of sample A in plot 3 of FIG. 8 is predominantly 81 angstroms and the pore radius of sample B in plot 3 of FIG. 8 is predominantly 55 angstroms. This corresponds with the pore size distributions obtained from plots 1 and 2. A summary of the appropriate test conditions is provided at Table 5.

It will be noted that a discontinuity appears in the plots of FIGS. 5 and 7 at a pressure of about 140 mmHg. These discontinuities are a consequence of the autoranging effect of the A/D converter used in generating FIGS. 4 to 8 and are not caused by the raw data which are used as a basis of the calculation.

TABLE 5

| Sample Type | A | B | A & B |
|---|---|---|---|
| Sample weight (g) | 0.36 | 0.42 | 0.24 |
| Sample density (g/cc) | 2.1 | 2.0 | 2.0 |
| Sample saturation pressure (mm Hg) | 760 | 773 | 771 |
| Desorbate | N₂ | N₂ | N₂ |
| Desorbate mass flow rate (ml/min) | 0.284 | 0.284 | 0.170 |
| Chamber line vol. ($V_L$) (cc) | 36.80 | 36.80 | 36.80 |
| Chamber line temp. ($T_L$) (°K.) | 315 | 315 | 315 |
| Sample holder vol. ($V_{S.H.}$) (cc) | 21.60 | 21.60 | 21.60 |
| Liq. N₂ Bath temp. ($T_{S.H.}$) (°K.) | 77.3 | 77.3 | 77.3 |
| Partial pressure range (P/P$_s$) | 1.0–0 | 1.0–0 | 1.0–0 |
| Tot. no. of pressure/time Data points sampled | 19,200 | 20,380 | 51,300 |

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A method for determining the amount of a gaseous adsorbate adsorbed by a solid adsorbent which comprises:
    (a) providing an evacuated chamber of known volume and maintained at a known temperature with an outgassed sample of adsorbent present therein;
    (b) introducing gaseous adsorbate into said sample containing chamber at a known substantially constant mass flow rate for a time sufficient to obtain adsorption of at least a portion of said adsorbate by said adsorbent, said mass flow rate being not greater than the equilibration rate of adsorption of the adsorbate by the adsorbent and not greater than about 0.7 ml/min at standard temperature and pressure conditions;
    (c) establishing the equilibrium pressure of said adsorbate as it is introduced into said chamber as a function of time, said equilibrium pressure being the sampled chamber pressure; and
    (d) correlating the adsorbate sampled chamber pressure, the adsorbate mass flow rate, and the time needed to attain said sampled chamber pressure with the amount of adsorbate adsorbed by the adsorbate at said sampled chamber pressure.

2. The method of claim 1 wherein the volume and temperature of said chamber is maintained substantially constant during said adsorbate introduction.

3. The method of claim 1 wherein said adsorbate is continuously introduced into said chamber for a time sufficient to achieve an adsorbate partial pressure (P/P$_s$) therein of greater than about 0.2.

4. The method of claim 3 wherein said adsorbate is introduced into said chamber for a time sufficient to achieve an adsorbate partial pressure of greater than about 0.35.

5. The method of claim 3 wherein said adsorbate is introduced into said chamber for a time sufficient to achieve an adsorbate partial pressure therein of about 1.0.

6. The method of any one of claims 1 to 5 wherein the adsorbate mass flow rate is from about 0.05 to about 0.7 ml/min. at standard temperature and pressure conditions.

7. The method of any one of claims 1 to 5 wherein the adsorbate mass flow rate is from about 0.2 to about 0.5 ml/min. at standard temperature and pressure conditions and the fluctuation, if any, in said mass flow rate is not greater than about ±0.15% of said mass flow rate during introduction into said chamber.

8. The method of any one of claims 1 to 5 wherein the adsorbate mass flow rate is from about 0.2 to about 0.4 ml/min. at standard temperature and pressure conditions and the fluctuation, if any, in said mass flow rate is not greater than about ±0.15% of said mass flow rate during introduction of said adsorbate into said chamber.

9. The method of claim 1 wherein the adsorbate is nitrogen.

10. The method of claim 1 wherein the adsorbate is a chemisorbate.

11. The method of claim 1 wherein the adsorbate mass flow rate is determined by reference to a blank, wherein: (a) said evacuated chamber of know volume and temperature is provided in the absence of an adsorbent sample and the adsorbate is introduced at the same substantially constant mass flow rate as employed in claim 1 in the presence of said sample, while establishing the adsorbate equilibrium pressure within said chamber as it is introduced therein as a function of time, said adsorbate equilibrium pressure being the reference pressure; and (b) the mass flow rate is correlated from the chamber in reference pressure per unit time at conditions of known volume and temperature.

12. The method of claim 1 wherein the sampled chamber pressure as a function of time is established in a manner sufficient to record from about 100 to about 10,000 sampled chamber pressure data points during the course of said adsorbate introduction.

13. The method of claim 1 wherein the amount of adsorbate adsorbed by the adsorbent is expressed as a volume and the volume is correlated with the sampled chamber pressure to determine the surface area of the adsorbent.

14. The method of claim 1 wherein the surface area of the solid adsorbent can be from about 0.01 to abut 1500 m²/g.

15. A method for determining the amount of desorbate desorbed as a gas from a solid desorbent saturated with condensed desorbate which comprises:
   (a) providing a chamber of known volume and temperature with a previously outgassed sample of desorbent present therein having said desorbate condensed thereon and in equilibrium with a chamber atmosphere consisting of gaseous desorbate;
   (b) withdrawing said desorbate from said chamber at a known, substantially constant mass flow rate which is not greater than equilibration rate of desorption of the desorbate from the desorbent for a period at least sufficient to desorb condensed desorbate from any pores of the sample;
   (c) establishing the equilibrium pressure of said desorbate as it is withdrawn from said chamber as a function of time, said equilibrium pressure being the desorbate sampled chamber pressure; and
   (d) correlating the desorbate sampled chamber pressure, the desorbate mass flow rate, and the time needed to attain said sampled chamber pressure with the amount of desorbate desorbed at said sampled chamber pressure.

16. The method of claim 15 wherein the volume and temperature of said chamber is maintained substantially constant during said desorbate withdrawal.

17. The method of claim 15 wherein said desorbate is continuously withdrawn from said chamber for a period sufficient to achieve a desorbate partial pressure therein of less than about 0.2.

18. The method of claim 17 wherein said desorbate is withdrawn from said chamber for a period sufficient to achieve a desorbate partial pressure therein of less than about 0.1.

19. The method of claim 17 wherein said desorbate is withdrawn from said chamber for a period sufficient to achieve a desorbate partial pressure therein of less than about 0.04.

20. The method of any one of claims 15 to 19 wherein the desorbate mass flow rate is from about 0.2 to about 0.7 ml/min. at standard temperature and pressure conditions.

21. The method of any one of claims 15 to 19 wherein the desorbate mass flow rate is from about 0.2 to about 0.4 ml/min. at standard temperature and pressure conditions, and the fluctuation, if any, in said flow rate is not greater than ±0.15% of said desorbate mass flow rate during withdrawal from said chamber to a desorbate partial pressure of not less than 0.03.

22. The method of any one of said claims 15 to 19 wherein the desorbate mass flow rate is from about 0.2 to about 0.3 ml/min. at standard temperature and pressure conditions, and the fluctuation, if any, in said flow rate is not greater than ±0.15% of said desorbte mass flow rate during withdrawal from said chamber to a desorbate partial pressure of not less than 0.02.

23. The method of claim 15 wherein the desorbate is nitrogen.

24. The method of claim 15 wherein the desorbate mass flow rate is determined by reference to a blank wherein: (a) said evacuated chamber of known volume and temperature is provided in the absence of a desorbent sample, said chamber having said desorbate condensed therein, and said desorbate being withdrawn as a gas from said chamber at the same substantially constant mass flow rate as employed in claim 15 in the presence of said sample, while establishing the desorbate equilibrium pressure within said chamber as a function of time, said desorbate equilibrium pressure being the reference pressure; and (b) the desorbate mass flow rate is correlated from the change in reference pressure per unit time at conditions of known volume and temperature.

25. The method of claim 15 wherein the desorbate sampled chamber pressure as a function of time is established in a manner sufficient to record from about 500 to about 40,000 desorbate sampled chamber pressure data points during the course of said desorbate withdrawal.

26. The method of claim 15 wherein the amount of desorbate desorbed from the desorbent is expressed as a volume, and this volume is correlated with the sampled chamber pressure to determine the pore size distribution of the adsorbent.

27. The method of claim 15 wherein the surface area of the desorbent can be from about 0.01 to about 1500 m²/g.

28. An apparatus for determining the amount of a gas adsorbed by a solid adsorbent sample or desorbed from a solid desorbent sample which comprises:
   (1) means for defining at least one chamber of known constant volume to contain said solid sample and a gs to be introduced into or withdrawn from said chamber means;
   (2) means for continuously introducing a gas into or withdrawing a gas from said chamber means;
   (3) means for establishing the pressure of said gas as a function of time within said chamber means as it is introduced or withdrawn therefrom;
   (4) means for controlling the mass flow rate of said gas as it is being introduced or withdrawn from said chamber to be (a) substantially constant over the entire partial pressure range, of gas within said chamber, of at least from about 0.02 to about 1.0, and (b) not greater than the equilibration rate of adsorption of the gas by the adsorbent sample during said gas introduction, and not greater than the equilibration rate of desorption of the gas from the desorbent sample during said gas withdrawal;
   (5) means for evacuating a gas from said chamber means and through said control means during withdrawal of said gas from said chamber means; and
   (6) means for maintaining a known temperature of gas within said chamber to be substantially constant.

29. The apparatus of claim 28 wherein said control means is a mass flow controller containing an electronically actuated variable aperture for controlling the mass flow rate of said gas being introduced into or withdrawn from said chamber means.

30. The apparatus of claim 28 wherein said control means is capable of controlling the mass flow rate of said gas being introduced or withdrawn from said chamber means to be from about 0.05 to about 0.7 ml/min. at standard temperature and pressure conditions.

31. The apparatus of claim 28 wherein said control means is capable of controlling the mass flow rate of said gas to be from about 0.02 to about 0.5 ml/min. at standard temperature and pressure conditions and any fluctuation in said mass flow rate is not greater than about ±0.15% of said mass flow rate during said gas introduction or withdrawal.

32. The apparatus of claim 28 wherein said control means is capable of controlling the mass flow rate of said gas to be from about 0.2 to about 0.4 ml/min. at standard temperature and pressure conditions and any fluctuation in said mass flow rate is not greater than about ±0.15% of said mass flow rate.

33. An apparatus for determining the amount of gas adsorbed by an adsorbent sample solid or desorbed from a desorbent solid sample which comprises:

(1) means for defining at least one chamber of known volume, said chamber means being adapted to permit: (i) a gas to be introduced therein or withdrawn therefrom; (ii) a solid sample to be introduced therein or withdrawn therefrom; and (iii) containment of a vacuum therein;

(2) first conduit means in fluid communication with the chamber means defining an input path for introducing a gas into said chamber means and an output path for withdrawing gas from said chamber means, with a portion of the volume of said input path to the first conduit means constituting a portion of said chamber means of known volume during introduction of a gas into said chamber means and a portion of the volume of said output path of the first conduit means constituting a portion of the chamber means of known volume during withdrawal of the gas from said chamber means;

(3) vacuum means for withdrawing a gas from said chamber means engaged in series and in fluid communication with the output path of said conduit means;

(4) control means having an input and an output, capable of controlling the mass flow rate of said gas (a) to be substantially constant as it is continuously being introduced into or withdrawn from said chamber, and (b) to be not greater than the equilibration rate of adsorption of the gas by the adsorbent sample during said gas introduction, and not greater than the equilibration rate of desorption of the gas from a desorbent sample during said gas withdrawal, when the partial pressure of said gas within said chamber varies from about 0 to about 1 during said gas introduction and from about 1 to about 0.02 during said gas withdrawal; the input of said control means being engaged in series and in fluid communication with the input and output path of said first conduit means; and the output of said control means being (a) engaged in series and in fluid communication with the input path of said first conduit means, and (b) engaged in series and in fluid communication with the output path of said first conduit means upstream from said vacuum means, the combination of said chamber, first conduit, control, and vacuum means being referred to as Assembly A;

(5) pressure sensing means engaged in fluid communication with said chamber means for sensing the pressure of said gas as it is being introduced into or withdrawn from said chamber means;

(6) pressure recording means engaged with said pressure sensing means for recording the pressure sensed by said pressure sensing means as a function of time;

(7) valve means set within Assembly A for: (i) disengaging the fluid communication of the output path of said conduit means, including said vacuum means engaged therein, with the chamber means during introduction of gas into said chamber means; and (ii) disengaging the fluid communication of the input path of said first conduit means with the chamber means during withdrawal of said gas from said chamber means; and (8) means for controlling the temperature of said chamber means to be substantially constant.

34. The apparatus of claim 33 wherein said control means is a mass flow controller containing an electronically actuated variable aperture for controlling the mass flow rate of said gas being introduced into or withdrawn from said chamber means.

35. The apparatus of claim 33 wherein said control means is capable of controlling the mass flow rate of said gas being introduced or withdrawn from said chamber means to be from about 0.05 to about 0.7 ml/min. at standard temperature and pressure conditions.

36. The apparatus of claim 33 wherein said control means is capable of controlling the mass flow rate of said gas to be from about 0.2 to about 0.5 ml/min. at standard temperature and pressure conditions and any fluctuation in said mass flow rate is not greater than about ±0.15% of said mass flow rate during said gas introduction or withdrawal.

37. The apparatus of claim 33 wherein said control means is capable of controlling the mass flow rate of said gas to be from about 0.2 to about 0.4 ml/min. at standard temperature and pressure conditions and any fluctuation in said mass flow rate is not greater than about ±0.15% of said mass flow rate.

38. The apparatus of claim 33 which additionally comprises a gas supply means for intermittently supplying gas to the input path of said conduit means upstream of said control means for introduction into said chamber means.

39. The apparatus of claim 38 which additionally comprises means for outgassing a solid sample at elevated temperatures and under a vacuum using said vacuum means.

40. The apparatus of claim 39 wherein said chamber means comprises a sample holder section and a conduit section said sample holder section being removably attached to said conduit section and having a valve for containing a vacuum therein, and said conduit section forming a part of the output and input paths of said conduit means.

41. The apparatus of claim 40 wherein said removably attached sample holder section is engagable with said outgassing means.

42. The apparatus of claim 40 wherein said chamber means is of known constant volume, and said temperature control means is capable of maintaining the temperature of the sample holder section of said chamber means to be substantially constant.

43. The apparatus of claim 33 wherein said pressure recording means comprises a computer.

44. The apparatus of claim 33 wherein said control means comprises:

an enclosure having an exterior surface and defining an inner space;

means for controlling the temperature within said inner space to be subtantially constant;

second conduit means defining: (a) an input path, for directing the flow of a gas from an input port disposed at the exterior surface of said enclosure into said inner space, engaged in fluid communication and merged with the input and output paths of said first conduit means, and (b) an output path in fluid communication with said input path of said second conduit means for directing the flow of said gas out of said inner space to an output port at the exterior surface of said enclosure, engaged in fluid communication and merged with the input and output paths of said first conduit means;

elongate sensing conduit means disposed within said enclosure inner space having an interior channel for directing the flow of a gas therethrough and having an input and an output; the input of said sensing conduit being engaged in fluid communication with the input path of said second conduit means and the output of said sensing conduit being engaged in fluid communication with the output path of said conduit means, the diameter of said sensing conduit interior channel being not greater than 0.2 mm;

flow meter means disposed within said enclosure inner space and in contact with said sensing conduit for sensing a temperature differential induced by change in the mass flow rate of a gas passing from the input to the output of said sensing conduit, and for generating a first output signal representative of said temperature differential and proportional to the mass flow rate of said gas passing through said sensing conduit;

means for generating a reference second output signal proportional to a selected mass flow rate of a gas;

means disposed within said enclosure inner space for comparing the first and second output signals and generating a third output signal representative of the differen of said first and second output signals;

valve means, disposed within said enclosure inner space engaged with said sensing conduit downstream of said flow meter means and with the output path of said second conduit means for controllably disengaging the fluid communication between the sensing conduit and the output path of said second conduit means thereby permitting regulation of the mass flow rate of a gas passing from said sensing conduit to the output path of said second conduit means, said valve means being actuated by said third output signal;

means for permitting the temperature of a gas passing through the input path of said second conduit means to equilibrate with the substantially constant temperature of said enclosure inner space before said gas enters the sensing conduit means;

means for controlling the pressure of a gas as it enters the input of said sensing conduit means to be substantially constant.

45. The apparatus of claim 44 wherein said pressure sensing means is located within said enclosure inner space.

46. The apparatus of claim 44 wherein said chamber means comprises a sample holder section and a conduit section said sample holder section being removably attached to said conduit section and having a valve for containing a vacuum therein, and said conduit section forming a part of the output and input paths of said first conduit means with from about 96 to about 98% of the volume of said conduit section being located within said enclosure inner space for controlling the temperature of a gas present therein to be substantially constant.

47. The apparatus of claim 44 wherein in said control means the diameter of the interior channel of the sensing conduit is not greater than 0.05 mm.

48. The apparatus of claim 44 wherein said means for controlling the temperature of said enclosure inner space of said control means comprises:

vent means disposed within said enclosure for engaging said inner space in fluid communication with the atmosphere exterior to said enclosure, thereby permitting the enclosure inner space to receive air from or discharge air to the environment external to said enclosure;

means for sensing the temperature of the atmosphere within said enclosure inner space and for generating a first temperature output signal proportional to said temperature;

means for generating a second temperature output signal proportional to the difference between said first output signal and a reference signal representative of a selected temperature;

means for heating the atmosphere within said inner space actuated by said second output signal; and means for continuously circulating air from external to said enclosure within said inner space at a rate of from about 10 to about 75 times the volume of said inner space per minute.

49. The apparatus of claim 44 wherein the input path of said second conduit means is adapted to form a coil for permitting the temperature of a gas passing therethrough to equilibrate with the temperature of said inner space.

50. The apparatus of claim 44 wherein in said control means said flow meter means comprises:

a plurality of self-heating sensor element coils having adjacent ends positioned along the flow path of a gas flowing through said sensing conduit means externally of said sensing conduit means, one of said sensor elements being closer to one end of said sensing conduit means than another of said sensor elements, said sensor element coils being formed of temperature sensitive resistant wire wound around the outer surface of said sensing conduit means and sensing their own temperature as modified by changes in the mass flow rate of said gas;

means for heating said sensor elements;

means for detecting the temperature differential of said sensor elements induced by said mass flow rate change; and means for generating said first output signal.

51. The apparatus of claim 44 wherein in said control means said valve means is a thermal valve responsive to thermoexpansion of an actuator relative to a reference member.

52. The apparatus of claim 45 wherein a portion of the first conduit means engaged with said pressure sensing means is adapted to form a coil for permitting the temperature of a gas present therein to equilibrate with the temperature of said enclosure inner space.

53. The apparatus of claim 46 wherein the temperature control means for controlling the temperature of the sample holder section of said chamber means to be substantially constant comprises:

vessel means adapted to: (a) contain a liquid bath maintained at a substantially constant temperature, and (b) receive said sample holder section in said chamber means for immersing said sample holder section in said liquid bath;

liquid level control means for maintaining the level of said liquid bath, having the sample holder section immersed therein, to be substantially constant.

54. The apparatus of claim 53 wherein the liquid level control means comprises:

means for sensing the level of said liquid bath and generating a signal when the level of said bath deviates from a preselected level;

means for introducing fresh liquid into said bath actuated by said liquid level sensing means signal;

means for separating any vaporized fresh liquid from said fresh liquid prior to introduction of said fresh liquid into said bath.

* * * * *